(12) United States Patent
Bransky et al.

(10) Patent No.: US 9,682,375 B2
(45) Date of Patent: *Jun. 20, 2017

(54) FLUID SAMPLE ANALYSIS SYSTEM

(71) Applicant: Pixcell Medical Technologies Ltd., Yokneam Ilit (IL)

(72) Inventors: Avishay Bransky, Kyriat Tivon (IL); Liron Shlomo, Kibbutz Shomrat (IL)

(73) Assignee: Pixcell Medical Technologies Ltd., Yokneam Ilit (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/198,287

(22) Filed: Jun. 30, 2016

(65) Prior Publication Data
US 2016/0346780 A1  Dec. 1, 2016

Related U.S. Application Data

(60) Continuation of application No. 14/950,323, filed on Nov. 24, 2015, now Pat. No. 9,404,917, which is a
(Continued)

(51) Int. Cl.
*G01N 33/52* (2006.01)
*B01L 3/00* (2006.01)
(Continued)

(52) U.S. Cl.
CPC ......... *B01L 3/50273* (2013.01); *B01L 3/5027* (2013.01); *B01L 3/502715* (2013.01);
(Continued)

(58) Field of Classification Search
CPC .... G01N 35/04; G01N 31/10; G01N 35/1081; G01N 2035/0415; G01N 15/1404;
(Continued)

(56) References Cited

U.S. PATENT DOCUMENTS

| 5,534,891 A | 7/1996 | Takano |
| 7,922,971 B2 | 4/2011 | Bryer et al. |
| (Continued) | | |

FOREIGN PATENT DOCUMENTS

| JP | 09-126989 | 5/1997 |
| JP | 09-318523 | 12/1997 |

OTHER PUBLICATIONS

Bransky, Avishay et al., "An automated cell analysis sensing system based on a microfabricated rheoscope for the study of red blood cells physiology," Biosensors and Bioelectronics 22(2): 165-169 (2006).
(Continued)

*Primary Examiner* — Hoa Pham
(74) *Attorney, Agent, or Firm* — Finnegan, Henderson, Farabow, Garrett & Dunner, LLP

(57) ABSTRACT

A fluid analysis system may include a stage configured to receive a sample holder including a fluid sample to be analyzed. The fluid analysis system may also include a fluid analyzer configured to monitor at least one characteristic of the fluid sample to be analyzed; and an inclined rail; wherein the stage is configured to move along the inclined rail to cause the sample holder to move with a first component of motion along an analysis axis of the fluid analyzer and simultaneously with a second component of motion orthogonal to the analysis axis of the fluid analyzer, wherein the first component of motion affects a focus of the fluid analyzer relative to at least one constituent of the fluid sample to be analyzed.

16 Claims, 22 Drawing Sheets

Related U.S. Application Data division of application No. 14/724,511, filed on May 28, 2015, now Pat. No. 9,222,935.

(51) Int. Cl.
*G01N 35/00* (2006.01)
*G01N 21/05* (2006.01)
*G01N 21/51* (2006.01)
*G01N 33/53* (2006.01)
*G01N 35/04* (2006.01)

(52) U.S. Cl.
CPC ..... *G01N 33/521* (2013.01); *G01N 35/00029* (2013.01); *B01L 2200/0684* (2013.01); *B01L 2300/0609* (2013.01); *B01L 2300/0816* (2013.01); *B01L 2300/0864* (2013.01); *B01L 2300/0867* (2013.01); *B01L 2300/0883* (2013.01); *B01L 2400/0406* (2013.01); *B01L 2400/0478* (2013.01); *B01L 2400/0481* (2013.01); *B01L 2400/0493* (2013.01); *G01N 21/05* (2013.01); *G01N 21/51* (2013.01); *G01N 33/5302* (2013.01); *G01N 35/04* (2013.01); *G01N 2021/058* (2013.01); *G01N 2021/513* (2013.01); *G01N 2035/00039* (2013.01)

(58) Field of Classification Search
CPC .. G01N 33/49; G01N 33/4875; Y10T 436/25; Y10T 436/113332
USPC ......... 356/244, 246, 440; 422/68.1, 521, 50; 414/751.1; 436/95, 128
See application file for complete search history.

(56) References Cited

U.S. PATENT DOCUMENTS

| | | | |
|---|---|---|---|
| 8,481,330 B2 | 7/2013 | Matsuda et al. | |
| 8,780,181 B2 | 7/2014 | Olesen et al. | |
| 8,889,424 B2 | 11/2014 | Ehrenkranz et al. | |
| 9,115,610 B2 * | 8/2015 | Tewes | F01L 1/344 |
| 9,222,935 B1 * | 12/2015 | Bransky | G01N 33/521 |
| 9,404,917 B1 * | 8/2016 | Bransky | G01N 33/521 |
| 2002/0142483 A1 | 10/2002 | Yao et al. | |
| 2004/0070757 A1 | 4/2004 | Moore et al. | |
| 2004/0239916 A1 | 12/2004 | Seino et al. | |
| 2006/0236958 A1 | 10/2006 | Sun et al. | |
| 2007/0041877 A1 | 2/2007 | Maurer et al. | |
| 2012/1016830 | 7/2012 | Hunter | |
| 2014/0026727 A1 | 1/2014 | Walter | |
| 2014/1024370 | 8/2014 | Iddon at at | |
| 2014/1035694 | 12/2014 | Bransky et al. | |

OTHER PUBLICATIONS

Bransky, Avishay et al., "Correlation between erthyrocytes deformability and size: A study using a microchannel based cell analyzer." Microvascular Research 73(1):7-13 (2007).

Bransky, Avishay et al., "The rheologic properties of erythrocytes: a study using an automated rheoscope," Rhelogica Acta 46(5): 621-627 (2007).

Chirila, T.V. et al., The Use of Hydrophilic Polymers as Artific lal Vitreous, Prog. Polym. Sci., 1998, vol. 23, pp. 475-508.

Clasen, C. et al., Determination of visoelastic and rheo-optical material functions of water-soluble cellulose derivatives. Prog. Polym. Sci., 2001, vol. 26, p. 1839-1919.

Faivre, Magalie et al., "Geometrical focusing of cells in a microfluidic device: an approach to separate blood plasma," Biorheology 43(2): 147-159 (2006).

Heidemann, S.R., et al., Towards a regional approach to cell mechanics, TRENDS in Cell Biology, 2004, vol. 14, No. 4, pp. 60-166.

Ho, B.P. et al., "Migration of rigid spheres in a two-dimensional unidirectional shear flow of a second-order fluid," Journal of Fluid Mechanics 76(4): 783-799 (1976).

International Search Report of PCT/IL2008/000772 mailed Jan. 21, 2009.

Joseph, D.D. et al., Motion of particles Setting in a Viscoelastic Fluid, Proceedings of the Second International Conference on Multiphase Flow. Kyoto, Japan, Apr. 3-7, 1995 (pp. 1-9).

Wu, Zhigang et al, "Rapid mixing using two-phase hydraulic focusing in microchannels," Biomedical Microdevices 7(1): 13-20 (2005).

Japanese Office Action mailed Jul. 1, 2014 for Japanese Application No. JP 2013-161659 and English Translation thereof (7 pages).

European Patent Office Communication dated Nov. 14, 2014 for European Application No. 08763530.6 (8 pages).

Tehrani, M.A., "An Experimental Study of Particle Migration in Pipe Flow of Viscoelastic Fluids," Journal of Rheology, vol. 40, No. 6, Jul. 26, 1996 (21 pages).

Matas, J.P. et al., "Lateral Forces on a Sphere," Oil & Gas Science and Technology, vol. 59, No. 1, Jan. 2004 (12 pages).

* cited by examiner

FLUID SAMPLE ANALYSIS SYSTEM

This is a continuation of U.S. application Ser. No. 14/950,323, filed Nov. 24, 2015, which is a divisional of U.S. application Ser. No. 14/724,511, filed May 28, 2015(which has issued as U.S. Pat. No. 9,222,935), all of which are incorporated herein by reference.

TECHNICAL FIELD

This present application relates to a fluid sample analysis system. Some embodiments may include a point-of-care testing (POCT) system including a unit for interacting, with a fluid sample cartridge and a focusing assembly for adjusting a position of the fluid sample relative to an analyzer,

BACKGROUND

Point-of-care testing includes medical testing at or near the site of patient care, such as at a doctor's office or on-site patient testing lab. A significant advantage of point-of-care testing is that tests (e.g., blood tests, etc.) can be performed quickly and locally such that test results may be obtained and reviewed while a patient is present on site, Such point-of-care testing can eliminate the need for sending samples to an off-site laboratory, which typically involves delayed receipt of testing results, which can delay clinical management decisions.

While POCT systems can offer significant benefits in terms of convenience and rapidly available test results, in order to provide meaningful information, these systems need to produce accurate and reliable test results. Rapidly available on-site test results may be convenient, but they may have little clinical value if they are error prone or if they experience significant variation from measurement to measurement. POCT systems often rely upon the use of disposable elements for capturing and retaining a sample for analysis. Such disposables can vary from one another and can introduce imprecision into the system, as a different disposable may be introduced for each new measurement. Thus, there is a need for POCT units capable of adapting to the variations introduced into the measurement system and analysis through interaction with disposable elements.

Some POCT systems may involve optical testing and may include optics that can be focused in order to improve the signal to noise ratio of optical measurements. With variations in disposable units (e.g., introduced through manufacturing variations, variation in placement of the disposable within the analysis system, etc.), the optics in a POCT system may require focusing each time a different disposable is introduced into the system, or even during some types of measurements. In some cases, focusing mechanisms may include highly accurate stepper or actuator systems (e.g., piezoelectric-based systems). While these systems may offer the desired accuracy, they can introduce added expense and complexity into the system.

SUMMARY OF THE INVENTION

One aspect of the disclosure may include a fluid analysis system, which may include a stage configured to receive a sample holder including a fluid sample to be analyzed. The fluid analysis system may also include a fluid analyzer configured to monitor at least one characteristic of the fluid sample to be analyzed; and an inclined rail; wherein the stage is configured to move along the inclined rail to cause the sample holder to move with a first component of motion along an analysis axis of the fluid analyzer and simultaneously with a second component of motion orthogonal to the analysis axis of the fluid analyzer, wherein the first component of motion affects a focus of the fluid analyzer relative to at least one constituent of the fluid sample to be analyzed.

Another aspect of the present disclosure may include a method for analyzing a fluid sample. The method may include moving a sample holder, including the fluid sample, along an inclined rail to a plurality of different locations along the inclined rail, wherein the movement of the sample holder results in a first component of motion of the sample holder along an analysis axis of a fluid analyzer, which is configured to monitor at least one characteristic of the fluid sample, and a second component of motion of the sample holder orthogonal to the analysis axis; acquiring images at each of the plurality of different locations along the inclined rail; analyzing the acquired images and automatically determining at least one indicator of focus quality at each of the plurality of different locations; determining a target position for the sample holder along the inclined rail based on the determined indicators of focus quality at the plurality of different locations; causing the sample holder to move to the target location; and analyzing the fluid sample at the target location.

Another aspect of the present disclosure may include a fluid analysis system. The fluid analysis system may include a stage configured to receive a sample holder including a fluid sample to be analyzed; and an activation unit including a rotatable camshaft and one or more cams associated with the camshaft. The one or more cams may be configured to: cause at least some movement of fluid associated with the sample holder upon rotation of the camshaft; cause fluid to flow back and forth between two fluid reservoirs on the sample holder by alternatingly pressing on pressable portions associated with the two fluid reservoirs upon rotation of the camshaft; and cause pressure against at least one fluid conduit associated with the sample holder in order to pinch the at least one fluid conduit closed.

DETAILED DESCRIPTION

The disclosed embodiments may include an analysis system that can receive a disposable cartridge/sample holder for performing a test on a fluid sample contained in or otherwise included on the cartridge. The cartridge may include one or more liquid reagents that can be stored in separate compartments. During the testing process, the analysis system may control the flow of reagents (e.g., between different areas of the cartridge) and the mixing of reagents (e.g., mixing of different types of reagents with one another and/or mixing of reagents with one or more samples, such as a sample fluid, for analysis). In some embodiments, the mixing and flow control may be achieved without physically contacting the reagents or samples. After a sample has been mixed with appropriate reagents and prepared for measurement, the analysis system may cause the prepared sample (e.g., cells suspended in a fluid) to flow into an analysis chamber, such as a transparent measurement chamber, where analysis of the sample may be performed. In some cases, the analysis may include microscopic imaging of cells or other types of particles in the prepared sample fluid. To perform the imaging, the analysis system may adjust the position of the analysis chamber relative to the optics of the imaging unit such that the cells or particles suspended in the prepared sample fluid are in optical focus.

Figure 1:
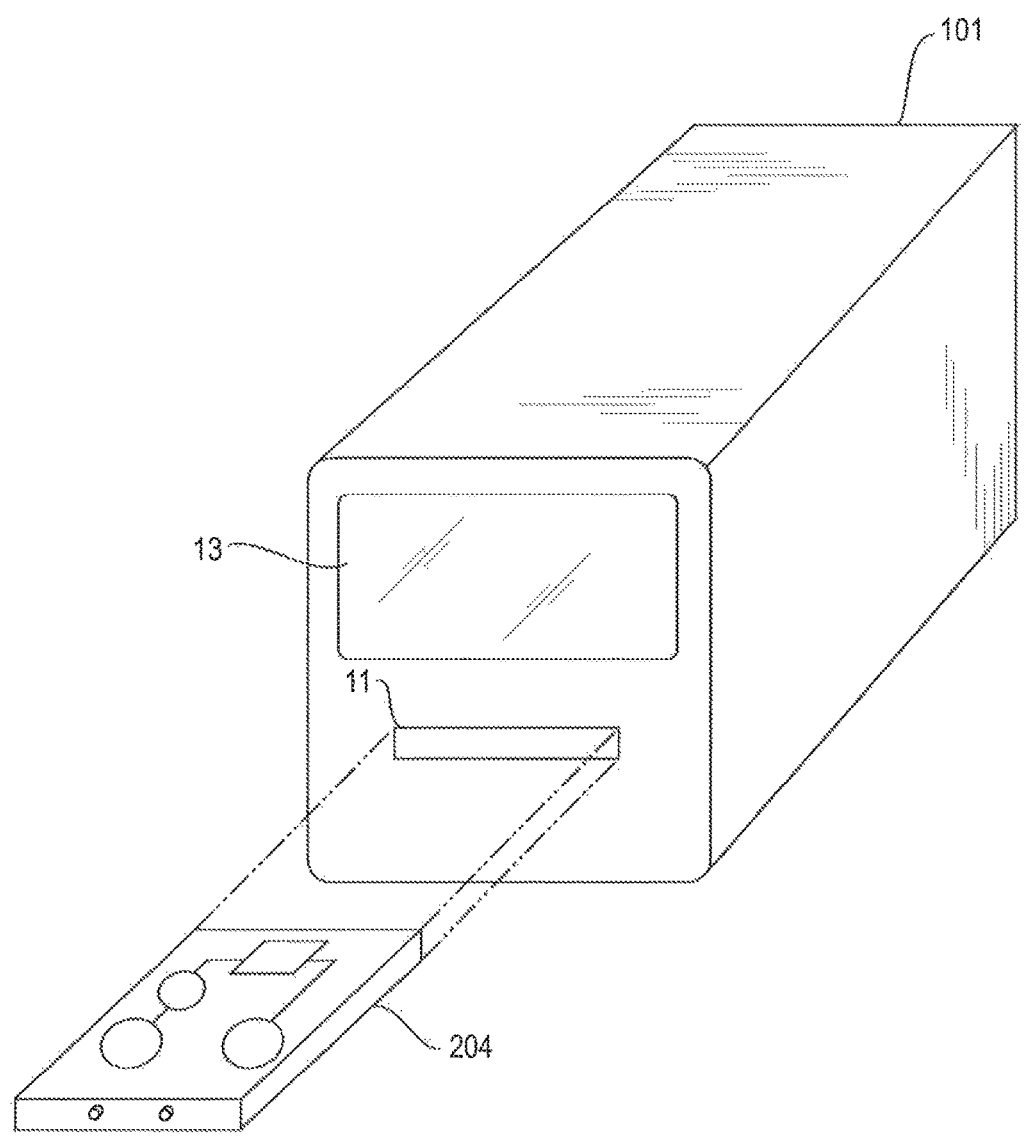
FIG. 1 provides a diagrammatic representation of an analysis system, according to exemplary disclosed embodiments.

FIG. 1 provides a diagrammatic representation of an analysis system 101, according to exemplary disclosed embodiments. In some embodiments, analysis system 101 may be a POCT unit for analyzing a fluid sample. The sample to be analyzed may be collected. and introduced to a cartridge 204, which may be inserted into a receiver 11 in analysis system 101 prior to the analysis process. Results of the analysis may be provided on a display 13. An operator of analysis system 101 may interact with the system via one or more input devices, which may include instances where display 13 includes a touch-sensitive device. Other input/output devices, such as keyboards, point devices, voice recognition units, etc. may be used to provide an operator with the ability to interact with and provide commands to analysis system 101.

Figure 2:
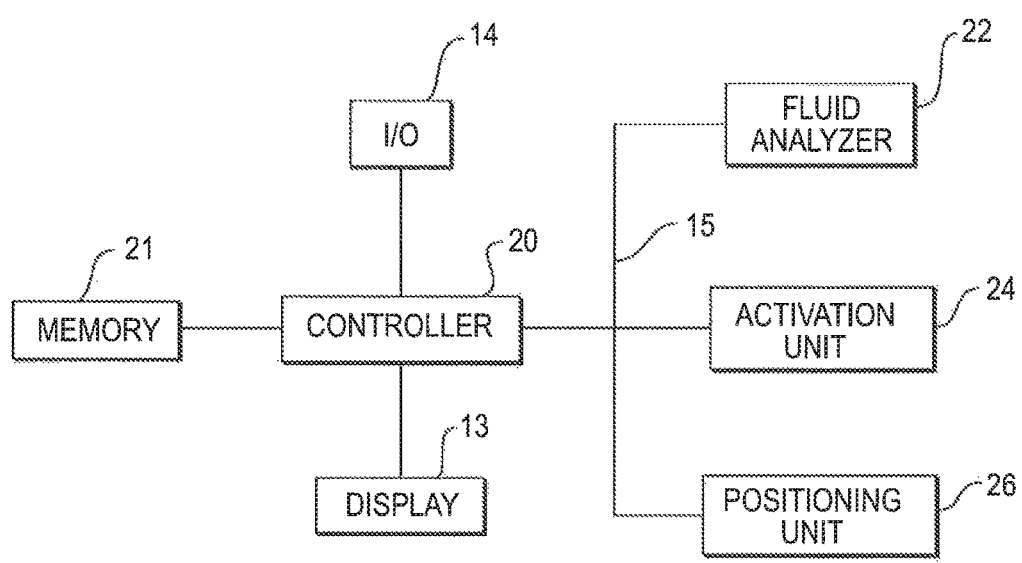
FIG. 2 provides a block. diagram representation of an analysis system, according to exemplary disclosed embodiments.

FIG. 2 provides a block diagram representation of components that may be included in analysis system 101, according to exemplary disclosed embodiments. For example, analysis system 101 may include a controller 20 connected either directly or indirectly to various components of analysis system 101. Controller 20 may have access to a memory 21 and may render text and/or images on display 13. In some cases, where display 13 includes a touch-sensitive device, controller 20 may receive user commands via the touch-sensitive device associated with display 13. Controller 20 may receive user input and provide various types of output via input-output (I/O) devices 14, which as noted may include various keyboards, point devices, voice recognition units, etc. Controller 20 may also be connected, for example, via a data bus 15, to a fluid analyzer 22, a cartridge activation unit 24, and a cartridge positioning unit 26.

Memory 21 may include any suitable type of data storage device and may include one or more data storage devices either of the same type or of different types. In some cases, memory 21 may include volatile or nonvolatile memory units. Memory 21 may include, e.g., any combination of RAM, ROM, SRAM, DRAM, PROM, EPROM, EEPROM, magnetic computer readable media, optical computer readable media, flash memory, FPGAs, etc.

Memory 21 may include various types of data and instructions accessible to controller 20. For purposes of this disclosure, references to a controller configured to or programmed to perform certain tasks or functions indicates that memory 21 has been populated with specific data and/or machine executable instructions such that controller 20 can execute those certain tasks or functions by accessing the data and/or instructions and executing one or more instructions included in memory 21. In some cases, memory 21 may include a device separate from controller 20, In other instances, memory 21 may be integrated with controller 20.

Controller 20 may include any suitable logic-based device capable of executing one or more instructions. For example, controller 20 may include one or more digital signal processors, microcontrollers, CPUs, etc. Controller 20 may execute x86 or ARM based instructions or instructions from any other suitable architecture, Controller 20 may include only a single integrated circuit or processing unit or may include multiple integrated circuits or processing units. For example, controller 20 may include one or more applications processors, touch processors, motion control units, video processors, etc.

Controller 20 may have various functions within system 101. For example, in some embodiments, controller 20 may include electronics and logic for operating or interacting with various components of system 101, including motors, lighting units, sensors. In certain embodiments, such components may include a pump for aiding in movement of fluids to different parts of a sample holder, pressure gauges, photodiode sensors, LEDs for lighting of a sample fluid, cameras or other types of image acquisition devices for capturing images of a sample fluid. In some embodiments, controller 20 may also interact with or control such components as a touch screen or keyboard and may run various algorithms for implementing processes or functions associated with system 101, including, for example, an autofocus process, image acquisition, processing of acquired sample fluid images, cell counting, cell classification, preparation of a sample fluid in a sample holder, movement of a sample holder to a suitable analysis position within system 101, movement of fluids within a sample holder, among other processes and functions.

Figure 3:
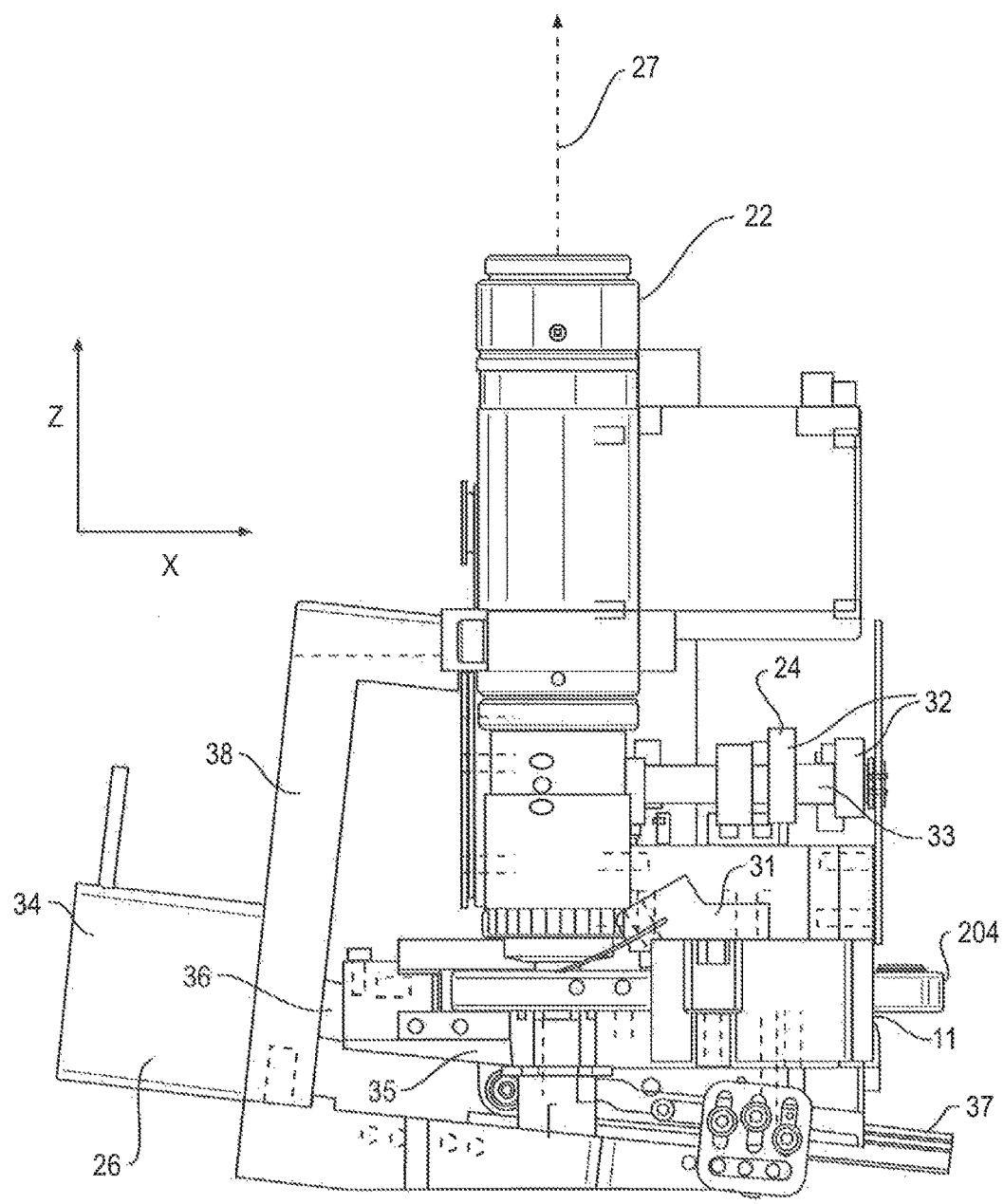
FIG. 3 provides a diagrammatic, side view representation of selected internal components of an analysis system, according to exemplary disclosed embodiments.

FIG. 3 provides a diagrammatic, side view of selected internal components of analysis system 101. For example, cartridge 204 may be introduced into analysis system 101 via receiver 11. In some embodiments, upon insertion of cartridge 204 into system 101, a cartridge holder 31 may retain and otherwise secure cartridge 204 in a desired location within analysis system 101. To prepare a sample included on cartridge 204, activation unit 24 may interact with one or more sections of cartridge 204 in order to prepare the fluid sample for analysis. In some embodiments, cartridge activation unit 24 may include one or more cams 32 incorporated on a rotating camshaft 33 in order to press (either directly by contacting sections of the cartridge or indirectly by interacting with one or more pistons (or any other suitable structures) that contact the cartridge) sections of the cartridge to prepare, mix, move, distribute, etc. a sample for analysis.

Positioning unit 26 may include various components for controlling the position of the prepared sample (e.g., on cartridge 204) relative to analysis components included in fluid analyzer 22. For example, in some embodiments, positioning unit 26 may include a motor 34 connected to a stage 35 via a shaft 36. When inserted into analysis system 101. cartridge 204 may be supported either directly or indirectly by stage 35. For example, cartridge holder 31 may include one or more elements to exert a force on cartridge 204 in order to secure cartridge 204 in place on stage 35. Motor 34 may be used to rotate or otherwise move shaft 36 in order to move stage 35. In some cases, stage 35 may be mounted on an inclined rail 37. In such embodiments, control of motor 34 may cause stage 35, and any components coupled to the stage, such as a retained cartridge, for example, to move along inclined rail 37. As a result of the movement along rail 37, stage 35 may simultaneously move both in the X direction and the Z direction relative to fluid analyzer 22.

Fluid analyzer 22 may be mounted to a frame assembly 38, to which motor 34 and inclined rail 37 may also be mounted. Fluid analyzer 22 may include one or more devices for analyzing a fluid sample contained within or included on cartridge 204. In some cases, fluid analyzer 22 may include components for performing flow cytometry based on laser scattering, fluorescence, impedance measurements, etc. Alternatively or additionally, fluid analyzer 22 may include an optical imager, including, for example, lenses, image sensors, and other components suitable for acquiring optical images of the sample. For example, in some embodiments, fluid analyzer 22 may include an optical sensor (such as a CCD, CMOS or photo-multiplier). One or more excitation sources (not shown) may be provided for illuminating a sample fluid to be analyzed with radiation having a wavelength suitable for a selected type of analysis. In some embodiments, the optical sensor may include a camera which acquires images of cells or particles flowing inside an inspection area of cartridge 204. Acquired images may then be processed by controller 20 using suitable software and/or hardware in order to determine, for example, a cell count for one or more cell types present in the sample fluid (e.g., neutrophils, lymphocytes, erythrocytes, etc.). Acquired images, image streams, analysis results, acquired or calculated data, etc. determined or obtained as part of the analysis process may be stored, for example, in memory 21. Detailed descriptions of each of the fluid analyzer 22, activation unit 24, and positioning unit 26 and the role of each in performing analysis of a fluid sample are included in sections below.

Cartridge

As noted, the disclosed embodiments may include a cartridge 204 for preparing a sample fluid for analysis. The sample fluid may contain particles of interest, such as cells, The sample fluid may include a bodily fluid including, for example, blood, cerebrospinal fluid (CSF), pericardial fluid, pleural fluid, or any other fluid that may contain cells. Any type of cells (or other particles) may be analyzed. In some cases, cells to be analyzed may include prokaryotic cells (e.g., bacteria); eukaryotic cells (e.g., red blood cells); white blood cells (Leukocytes); epithelial cells; circulating tumor cells; cellular fragments (e.g., platelets); or others.

In some embodiments, cartridge 204 may be used for preparing a blood sample for optical analysis to provide a Complete Blood Count (CBC). It should be noted, however, that the disclosure is not limited to CBC. Disposable cartridges in accordance with the disclosure may be used for multiple applications where analysis of cells is desired, such as HIV monitoring (such as using CD4/CD8 ratio), detection of f-hemoglobin, Malaria antigen or other blood parasites, Paroxysmal Nocturnal Hemoglobinuria (PNH), diagnosis of Celiac disease using Intestinal Endomysial Autoantibodies (EmA), Alzheimer's disease, or any other application for which cell-based diagnosis may be relevant.

Figure 4:
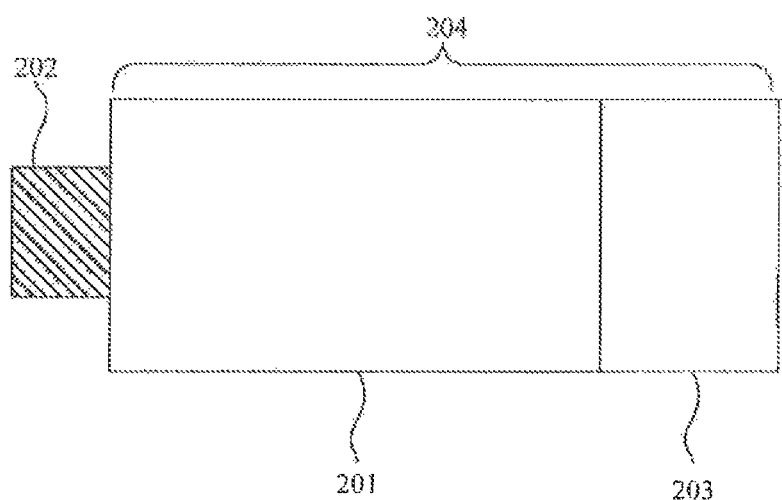
FIG. 4 provides a diagrammatic representation of a cartridge 204, according to exemplary disclosed embodiments.

FIG. 4 schematically illustrates a cartridge 204 according to certain embodiments of the disclosure. A sampler 202, which may function to introduce a sample fluid into the cartridge may be inserted into the cartridge 204, e.g., from one side. The sample fluid may be received by a preparation compartment 201 where one or more processes may be performed relative to the sample fluid to prepare the sample fluid for analysis. An analyzing compartment 203 may be coupled to the preparation compartment 201. The analyzing compartment may receive the prepared sample fluid from the preparation compartment 201 and may enable analysis of one or more aspects of the sample fluid. In some embodiments, the preparation compartment 201 and the analyzing compartment 203 may be separately formed and coupled together by one or more flow paths, in some embodiments, the cartridge preparation compartment 201 and the analyzing compartment 203 may be manufactured together and coupled during, or immediately after manufacturing, or they may be manufactured separately and become coupled prior to marketing the cartridge to its end user or even just prior to usage thereof, possibly even by a person performing the test or automatically inside system 101. A pump (not shown) may serve to generate a pressure gradient, such as vacuum, that drives a flow of a sample fluid within and between various sections of the cartridge.

In some embodiments, the preparation compartment 201 and the analyzing compartment 203 may include two separate compartments coupled together. In other embodiments, however, the preparation compartment 201 and analyzing compartment 203 may comprise integral parts of cartridge 204. For example, in some embodiments, preparation compartment 201 and analyzing compartment 203 may be integrally formed relative to a common substrate. Additionally, the sampler and the analyzing compartment may be positioned, with reference to cartridge 204, in any suitable orientation or layout arrangement depending on the requirements of a particular application.

In some embodiments, sampler 202 may be formed as an integral part of cartridge 204. In other embodiments, however, sampler 202 may be formed as a component separate from cartridge 204. In either case, however, sampler 202 may include a carrier for holding a sample fluid. The carrier may include, for example, one or more capillary tubes that may be used to collect a fluid sample. According to certain embodiments, system 101 may automatically couple the sampler 202 to the cartridge 204 in order to introduce the sample fluid into cartridge 204.

Figure 5:
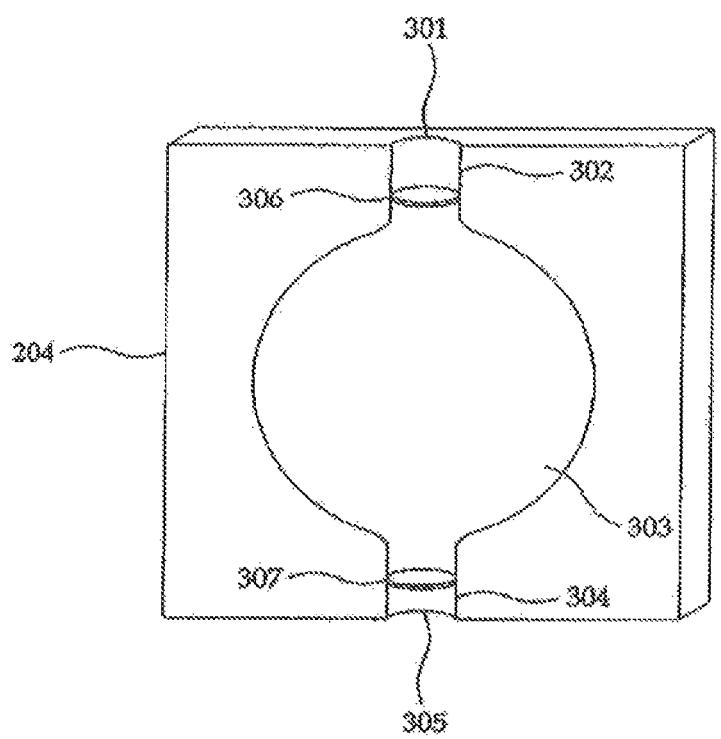
FIG. 5 provides a diagrammatic illustration of a section of a cartridge, according to exemplary disclosed embodiments.

FIG. 5 provides a diagrammatic illustration of a section of cartridge 204, according to certain embodiments. In the cartridge 204, a first opening 301, may be located in one of the sides thereof and may be configured for receiving a carrier carrying a sample fluid. A first channel 302 is coupled to the first opening 301 and to a reservoir 303. The reservoir 303 is configured to receive the sample fluid and to perform a procedure affecting it, thereby forming an output fluid. Then, the reservoir is configured to release the output fluid into the second channel 304, and therefrom out of the cartridge via a second opening 305. A preceding seal 306, configured to prevent flow from the reservoir via the first opening may be coupled to the first channel 302, and a succeeding seal 307, configured to prevent flow from the reservoir via the second opening, may be coupled to the second channel 304.

The term "output fluid" may include a fluid resulting from a procedure affecting the sample fluid. The fluid entering the reservoir, prior to the affecting procedure, may be referred to as an "input fluid." In some cases, the input fluid may correspond to a sample fluid introduced into reservoir 303, for example.

The procedure affecting a sample fluid, performed inside a reservoir, such as reservoir 303, may include any procedure that may provide a change of a physical or a chemical state (or a change of at least one property or characteristic) of the sample fluid or of the cells contained within the sample fluid. Examples of possible affecting procedures may include heating, mixing, diluting, staining, permeabelization, lysis, etc.

In certain embodiments of the disclosure, reservoir 303 may be pre-loaded with a substance. The pre-loaded substance may be a liquid substance, a solid substance or a combination thereof. The substance may consist of a single reagent or of several different reagents. An example of a liquid substance consisting of several reagents is PBS (Phosphate Buffered Saline), while examples of solid substances include lyophilized antibodies, different kinds of powdered stains dissolvable, e.g., in water or in ethanol, coated beads, etc. A substance may be lying free on the bottom of the reservoir or may be attached to an inner surface of the reservoir. Alternatively, a substance may be attached to structures or components, such as sponge or microfibers, filling the space of the reservoir. Such structures or components may enlarge an amount of surface area exposed to the sample fluid.

Furthermore, some possible procedures, such as heating, may not require having a pre-loaded substance in the reservoir. Therefore, in certain embodiments the reservoir is not pre-loaded with a substance, while it is possible that the reservoir holds instead (or in addition to a pre-loaded substance) a mechanism, such as a heating mechanism or part thereof in addition, understanding that pre-loading the substance may be performed during manufacturing of the cartridge or at any time prior to the introduction of the sample fluid, it can he appreciated that according to alternative embodiments, the substance may be introduced into the reservoir together with or after introducing the sample fluid. In other cases, wherein the substance is composed of a combination of constituents or wherein the substance is the outcome of a chemical reaction between more than one constituents, it is possible that at least one constituent is pre-loaded while at least one other constituent is introduced with or after introduction of the sample fluid.

Where reservoir 303 is loaded with a substance, whether pre-loaded or loaded with/after introduction of the sample fluid, the procedure affecting the sample fluid may include mixing of the sample fluid with the substance. In some cases, the sample fluid and the substance may be mixed thoroughly as a lack of homogeneity may impact subsequent analysis. According to certain embodiments of the disclosure, in order to enable mixing, at least part (a portion) of the surface of the reservoir, may include a pressable portion made of an elastic polymer, for example, polyurethane or silicone, or of a different elastic material. Due to deformation (such as constriction) of the reservoir, affected by pressing and/or releasing the pressable portion, fluid contained within the reservoir may form a jet flow inside the reservoir, which is a form of flow that may enhance mixing. Hence, according to embodiments of the disclosure, it may be possible to achieve mixing by alternatively pressing and releasing the pressable portion of the reservoir. When the pressable portion is pressed, the fluid may flow away from the pressed area, and when it is released, the fluid may flow back, such that the fluid flows back and forth.

In certain embodiments of the disclosure, a pressable portion may constitute a part of a reservoir's surface, for example, an upper surface of a reservoir or a certain percentage of its surface. In other embodiments of the disclosure, the entire reservoir may be pressable. For purposes of this disclosure, the term "pressable" refers to an ability of a material to deform, at least partially, in response to applied pressure to the material. In some embodiments, the deformation of the pressable material may result in a change of volume in a region contained, at least partially, by the pressable material.

Apart from or in addition to mixing, procedures affecting the sample fluid performed in the reservoir may include reactions that may occur between the substance and the sample fluid. The reaction may include a chemical reaction, for example oxidation/reduction, or a biochemical reaction such as binding antibodies to ligands. The procedure may lead to changes in physical and/or chemical states of the sample fluid or of cells contained within the sample fluid. For example, it may affect changes in viscoelastic properties or in pH of the sample fluid. A concentration of cells contained in a sample fluid may decrease due to dilution. A cellular membrane may become permeable enabling binding of coloring agents or antibodies contained within the substance to cellular components, such as cytoplasmic granules. An oxidation or reduction of different cellular components may happen, such as oxidation of hemoglobin contained in the red blood cells into methemoglobin, etc.

After the procedure has been completed (or at least partially completed), the resulting output fluid may be released from the reservoir. The releasing may be affected by positive pressure or "pushing" the fluid out of the reservoir. For example, fluid may be pushed out of the reservoir by pressing. Additionally or alternatively, the fluid may be affected by negative pressure, for example if fluid is driven out of the reservoir by physical forces the "pull" it out, such as gravitational force or due to application of external forces such as a vacuum. In certain embodiments of the disclosure, the flow of the output fluid from the reservoir via the second opening into the analyzing compartment may be caused by a suction force generated by the vacuum pump 104 coupled to the analyzing compartment, as shown in FIG. 1.

Reservoir 303 may be enclosed between two seals, wherein the preceding seal 306 prevents fluid from flowing out of the reservoir via the first opening 301 and the succeeding seal 307 prevents fluid from flowing out of the reservoir via the second opening. Prior to introduction of the sample fluid into reservoir 303, the two seals 306 and 307 may prevent release of substances from the reservoir. These seals may also prevent release of the substance and/or the sample fluid during an affecting procedure. And, the seals may prevent unintentional release of the output fluid.

Regarding seal 307, breaking or breaching of seal 307 may allow output fluid to flow out of the reservoir towards the second opening. In some embodiments, after breaching the seal, it may be left open. In some embodiments, the second seal 307 may constitute a breakable or "frangible seal." It is possible to form the seal, e.g., of adhesive configured to be to be broken by application of pressure exceeding a certain threshold. Applying pressure on the pressable part of a reservoir may result in a pressure at the position of the seal that exceeds the breaking threshold of the seal, which causes the seal to breach. The output fluid may then be released into the second channel 304, through the second opening 305 and into the analyzing compartment. in other words, the output flow may be conveyed to the analyzing compartment via the second channel 304 and the second opening 305.

Mixing of the sample fluid with the substance by intermittently pressing the pressable portion of the reservoir may not result in super-threshold pressure at the position of the seal. Thus, during mixing, the seal 307 may remain intact. In some embodiments, a structure or obstacle may be formed in a flow path prior to seal 307 to protect the seal from being affected by any super-threshold pressure that may be caused during mixing. For example, pressure may be applied on a channel between the reservoir and the seal, hence obtaining a physical obstacle preventing pressure arising in the reservoir to reach the seal. In other embodiments, super-threshold pressure may be allowed to reach the seal and breach it, however, a physical obstacle located on the channel may prevent fluid from flowing until the obstacle is removed.

Referring back to preceding seal 306, this seal may have different roles. In a first role, seal 306 may prevent the release of the substance from the reservoir prior to the introduction of the sample fluid. However, when introducing the sample fluid, the preceding seal must be broken, in order to allow such introduction. In some embodiments, in order to allow mixing using pressure provided to the pressable portion of the reservoir, the reservoir may be sealed from both sides, Therefore, the preceding seal 306 may also be resealable after introduction of the sample fluid. Re-sealing of the seal 306 may allow mixing while avoiding an unintentional release of the output fluid from the reservoir, e.g., via channel 302.

As noted, the sample fluid may be introduced via the first opening using a carrier. In embodiments wherein the carrier is left in the cartridge after introduction of the sample fluid, re-sealing may prevent passage of fluid via any gap existing between the carrier and the first channel's internal surface.

Figure 6B:
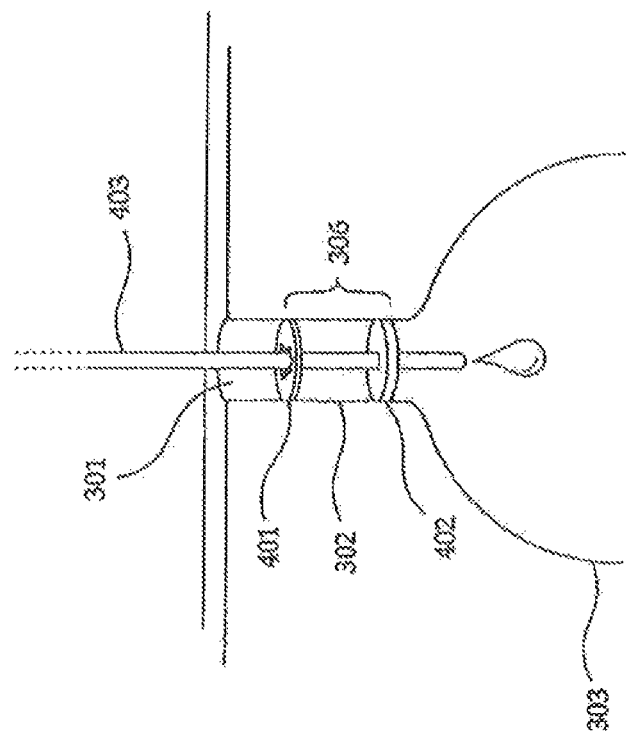
FIGS. 6A and 6B depict a seal, according to exemplary disclosed embodiments.
Figure 6A:
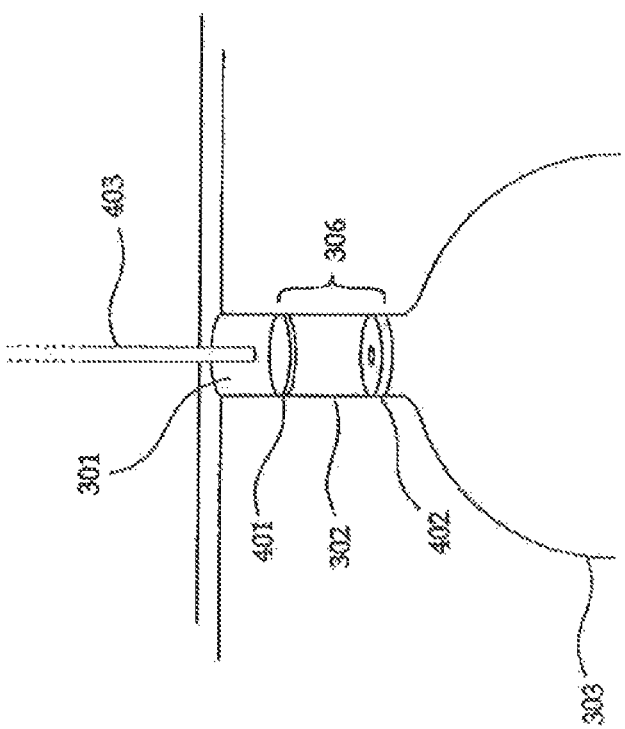

FIGS. 6A and 6B depict a preceding seal 306, according to certain embodiments of the disclosure. The embodiments shown in FIGS. 6A and 6B may be adapted for a carrier that remains inside the first channel subsequent to the delivery or introduction of the sample fluid.

In accordance with the illustrated embodiments, the depicted preceding seal 306 may be comprised of two separate seals, namely, a first seal 401 and a second seal 402. FIG. 6A depicts the preceding seal prior to introduction of the sample fluid using a carrier 403, while FIG. 6B depicts the seal when the carrier is inserted, penetrating the preceding seal 306. In some embodiments, carrier 403 may include a capillary associated with sampler 202.

The first seal 401 is configured to prevent flow from the reservoir via the first opening prior to introduction of the sample fluid (the first role mentioned above). Hence, similar to the succeeding seal, the first seal 401 may be a frangible seal, formed of adhesive or a plug. Upon insertion of the carrier 403 into the reservoir via the first opening, the carrier 403 breaks seal 401, as illustrated in FIG. 6B.

The second seal 402 may operate to re-seal the reservoir after the insertion of the carrier. The second seal may be configured to prevent the leakage through the interface between the carrier, more accurately, the outer surface of the carrier, and the inner surface of the channel. According to certain embodiments, the seal 402 may be comprised of a flexible ring mounted inside the channel (e.g., an o-ring). The inner diameter of the ring is smaller than the diameter of the carrier. Thus, while the seal 402 allows the carrier to pass through, it may close tight around the carrier to prevent leakage. According to alternative embodiments, the first seal 401 and the second seal 402 may be swapped, that is, seal 402 may appear prior to the first seal 401.

Carrier 403 may be hollow. Thus, after the insertion thereof, flow or leakage out of the reservoir may occur into or through the hollow, inner space of the carrier. This leakage may be prevented by a hydrophobic membrane located inside the carrier.

Figure 7B:
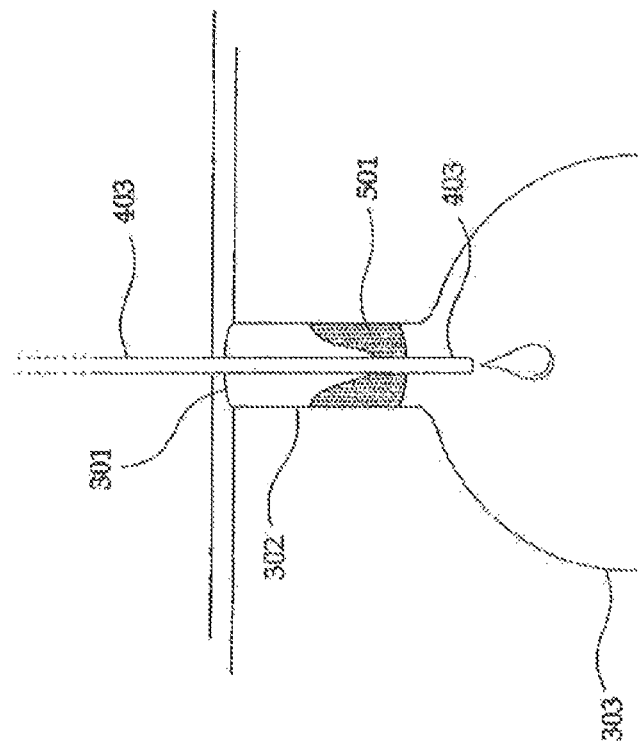
FIGS. 7A and 7B depict a seal, according to exemplary disclosed embodiments.
Figure 7A:
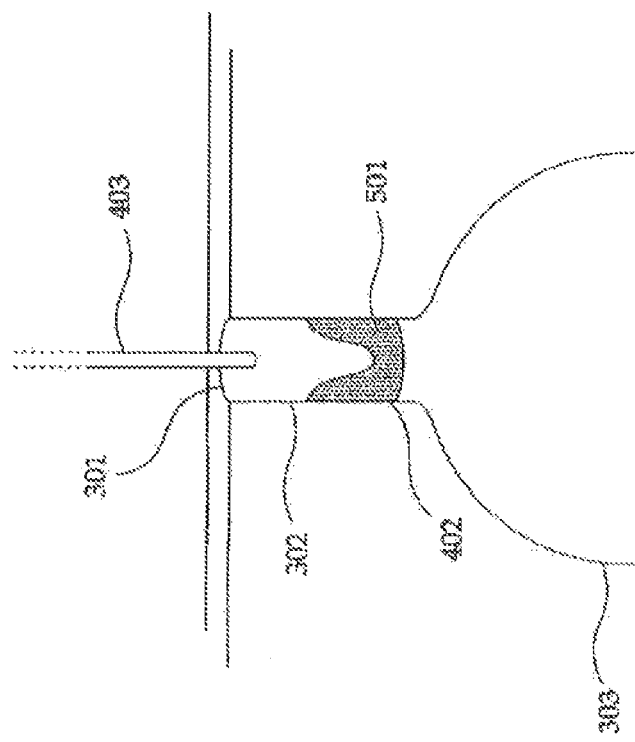

FIGS. 7A and 7B depict another preceding seal, according to certain embodiments of the disclosure. The seals shown in FIGS. 7A and 7B include a single member whose functionality is similar to the functionality of seals 401 and 402 in combination. For example, in FIG. 7A, a stopper 501 with centering shoulders is molded inside the first channel 302. Stopper 501 prevents flow from the reservoir via the first opening 301, prior to the introduction of the sample fluid. Upon insertion of a carrier 403, as illustrated by FIG. 7B, the center of the stopper 501 is breached, while the shoulders of the stopper block the interface between the outer surface of the carrier and the inner surface of the channel, preventing leakage further to the sample fluid introduction. According to certain embodiments, stopper 501 may be formed of a soft adhesive elastomer. Other materials may also be used to form stopper 501, however.

Certain embodiments may include a process of preparation of a sample fluid for analysis, for example, through interaction with cartridge 204 by activation unit 24 (described in more detail below). For example, a carrier 403 of a sample fluid may be inserted via the first opening 301 into the first channel 302. The carrier breaches the preceding seal 306 coupled to the first channel and delivers the sample fluid into the reservoir 303 (FIG. 6A). Inside the reservoir a procedure may be performed relative to the sample fluid, such as mixing the delivered sample fluid with a substance pre-loaded into the reservoir, thus obtaining an output fluid. Mixing may be enabled by applying an intermittent pressure on a pressable portion of the reservoir. Upon completion of the procedure, the succeeding seal 307 (FIG. 5) may be broken by pressing the reservoir in a manner that creates a super-threshold pressure at the position of the succeeding seal. The super-threshold pressure may result in opening of the seal 307 and a release of the obtained output fluid from the reservoir, The released output fluid may then flow via the second channel 304 and the second opening 305 into the analyzing compartment 203, wherein it can be subjected to analysis.

Figure 8:
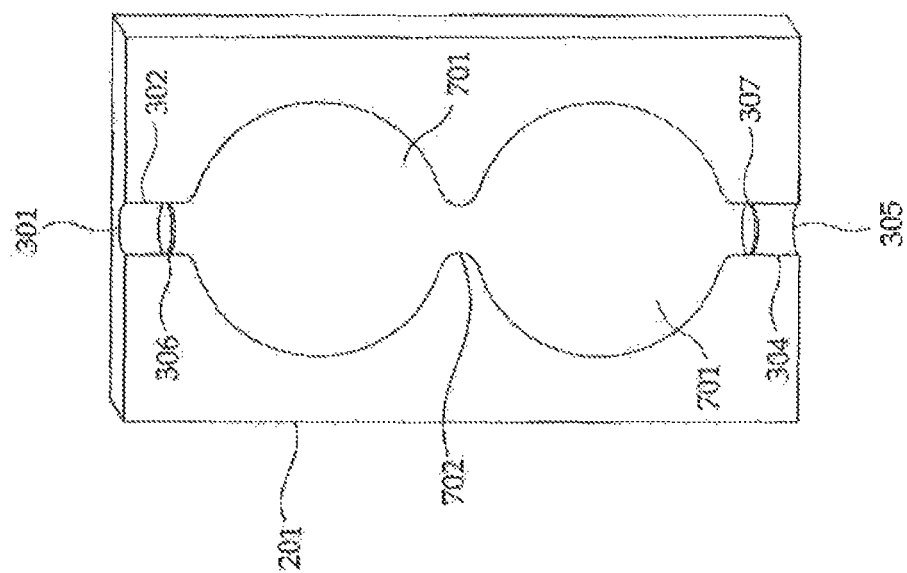
FIG. 8 provides a diagrammatic illustration of a section of a cartridge, according to exemplary disclosed embodiments.

FIG. 8 shows a section of a cartridge comprising a reservoir containing two compartments, according to certain embodiments of the disclosure. The two compartments 701, either or both of which may be pre-loaded with a substance, are interconnected by a flow path 702. The first compartment is coupled to the first opening 301 via a first channel 302, while the second compartment is coupled to the second opening 305 via a second channel 304. Either or both of the two of the compartments may include a pressable portion.

Where both compartments include pressable portions, it may be possible to achieve mixing by alternating pressure applied to the two pressable portions (e.g., one compartment and then the other). The flow path 702 between the compartments 701 may cause jet flow to occur, which may enhance mixing. Breaking the succeeding seal 307 may be caused, e.g., by simultaneously pressing both compartments and/or by applying stronger pressure than a pressure applied for mixing.

In case that there is only one pressable portion, on one of the compartments, it may be possible to achieve mixing by intermittently pressing this portion. Breaking the succeeding seal 307 may be caused by applying a super-threshold pressure on the pressable portion.

Figure 9:
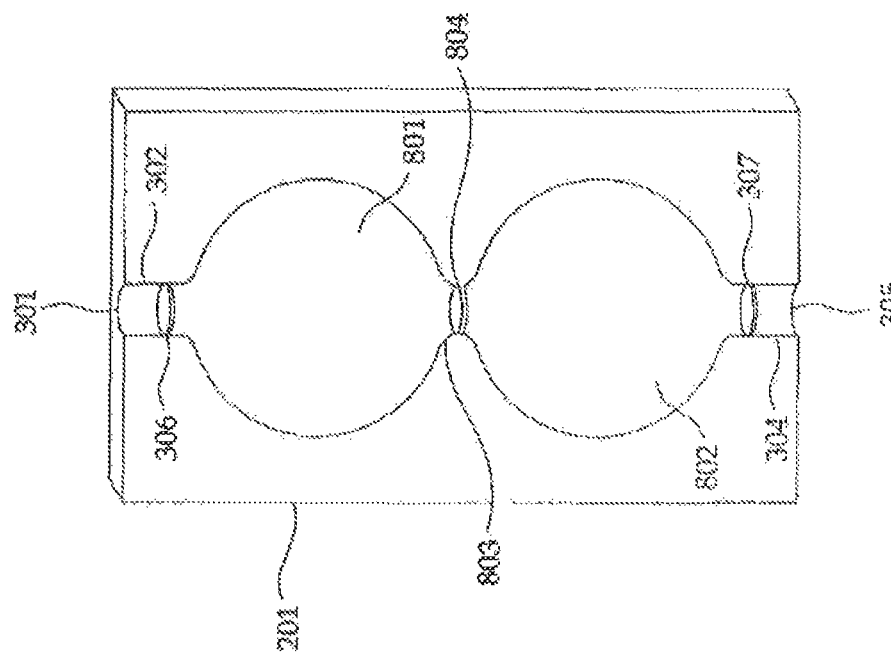
FIG. 9 provides a diagrammatic illustration of a section of a cartridge, according to exemplary disclosed embodiments.

FIG. 9 shows a section of a cartridge comprising a preparation unit composed of two reservoirs, according to certain embodiments of the disclosure. A first reservoir 801 coupled to a first opening 301 may comprise a pressable reservoir, while a second reservoir 802 coupled to a second opening 305, may comprise either a pressable or non-pressable reservoir. The two reservoirs may be connected by a connecting channel 803, which, in turn may be sealed by a seal 804. The two reservoirs may be located between seals 306 and 307, the first reservoir 801 being preceded by seal 306 and the second reservoir 802 being succeeded by a seal 307.

While each reservoir may be associated with a respective input fluid and a respective output fluid, the input fluid of the first reservoir 801, introduced thereto via the first opening, may include a sample fluid. Inside the first reservoir a procedure affecting the fluid may be performed. This procedure may be referred to as a "first procedure". By affecting appropriate pressure on seal 804 (e.g., a super-threshold pressure associated with seal 804), it may be breached resulting in release of the output fluid from the first reservoir 801 such that the output fluid is conveyed to the second reservoir 802. The output fluid of the first reservoir may serve as an input fluid of the second reservoir.

Where seal 804 is a frangible seal, once the seal has been breached the channel 803 between the two reservoirs 801 and 802 may remain open, and fluid flow may be possible in both directions between reservoirs 801 and 802 (i.e., from 801 to 802 and from 802 to 801). Where seal 804 includes a frangible seal, once that seal is breached, the two reservoirs may form, in effect, two compartments of a single reservoir. Therefore, in embodiments having a frangible seal in the connecting channel 803, after breaching this seal, the output fluid of the first reservoir 801 can flow back and forth between the two former reservoirs and may be affected by any procedure associated with reservoir 801 or reservoir 802 when the fluid resides in those compartments. Further, after breaching a frangible sea 804 to effectively form a single reservoir with two compartments, the channel 803 connecting the two compartments of the single reservoir may be referred to as coupling "compartment" 801 with "compartment" 802 and, therefore, with opening 305.

In other embodiments, for example, where seal 804 is re-sealable, after conveying the output fluid of reservoir 801 to reservoir 802, seat 804 may be resealed such that fluid may be precluded from traveling back to reservoir 801. An example of a re-sealable seal may include a valve. Alternatively or additionally, certain embodiments may include a re-sealable connecting channel 803, Where re-sealing may be performed, for example, by reintroducing pressure to the connecting channel 803 to physically block the opening of channel 803 and prevent fluid from flowing through channel 803.

Inside the second reservoir 802, a "second procedure" may be performed. By causing an appropriate pressure level on seal 307, that seal may be breached, thus resulting in release of the output fluid from the second reservoir 802 towards the second opening 305. The output fluid of the second reservoir may constitute an output fluid of the preparation unit formed based on reservoirs 801 and 802. The output fluid of the preparation unit may flow via the second opening 305 into an analyzing compartment (such as analyzing compartment 203 of FIG. 4), wherein it may be subjected to analysis.

Each reservoir in a preparation unit may be configured to perform or otherwise be associated with a particular procedure. For example, if a first reservoir obtains the sample fluid, the procedure associated with the first reservoir may affect this sample fluid, yielding a derivative of the sample fluid. The derivative may include a change having occurred in either or both of the sample fluid or in cells or components contained within the sample fluid. The change may include a chemical change, a biochemical change, a physical change, etc. Examples of a chemical change may include a change in pH, oxidation/reduction of cellular components or hinging of chemical agents, such as dyes thereto; examples of a biochemical change may include binding of antibodies to ligands; and examples of physical changes may include changes in viscoelastic properties, in temperature or in concentration of diluents. In some embodiments, the sample fluid may be considered as a derivative of itself, i.e., a derivative of the sample fluid. Hence, a procedure may obtain as input a derivative of the sample fluid and yield an output which is a derivative of the derivative. In such embodiments, an input to the reservoir may be referred to a first derivative of the sample fluid, and the output of the reservoir may be referred to as a second derivative of the sample fluid. The same reference scheme may be used to refer to all reservoirs in a preparation unit: each reservoir may obtain an input fluid which is a derivative of the sample fluid. A first process performed on the sample fluid may provide a first derivative of the sample fluid, a second process performed to the first derivative of the sample fluid may provide a second derivative of the sample fluid, and so on for each process associated with the reservoirs of a preparation unit.

Because the reservoirs may be consecutively arranged, the procedures may also occur consecutively. For example, the procedure of a certain reservoir in a series may yield a second derivative of the sample fluid, which becomes the output of the reservoir. The next reservoir may obtain the second derivative as an input from the preceding reservoir and provide a third derivative of the sample fluid. This chain may last, until the final reservoir conveys its respective derivative of the sample fluid towards the final opening. In some cases, the output of one reservoir is not merely passed in series to a following reservoir. Rather, in some cases, a seal, such as a frangible seal, between two reservoirs may be opened, and any fluid in the two reservoirs may mix to create a new derivative of the sample fluid. Notably, however, the new derivative may be shared across both of the two reservoirs (e.g., through a back and forth mixing process) such that at least some of the new derivative fluid resides in both reservoirs.

An example for consecutive procedures may include an immune-labeling of cells: labeling with a primary antibody may be performed in a first reservoir followed by a consecutive labeling with a secondary antibody, performed in a second reservoir. Another example may include differential staining of white blood cells of a blood sample, with two staining reagents, that must be separated during storage. A procedure of staining with a first reagent, performed in a first reservoir, may be followed by staining with a second reagent, performed in a consecutive, possibly last reservoir.

It should be appreciated that in accordance with embodiments of the present disclosure the procedure may be performed inside the reservoirs, wherein each reservoir adds a stage in the preparation of the output fluid, all together resulting in a cumulative continuous process. This process may result in efficient and complete mixing of the fluid and the reagents.

Figure 10A:
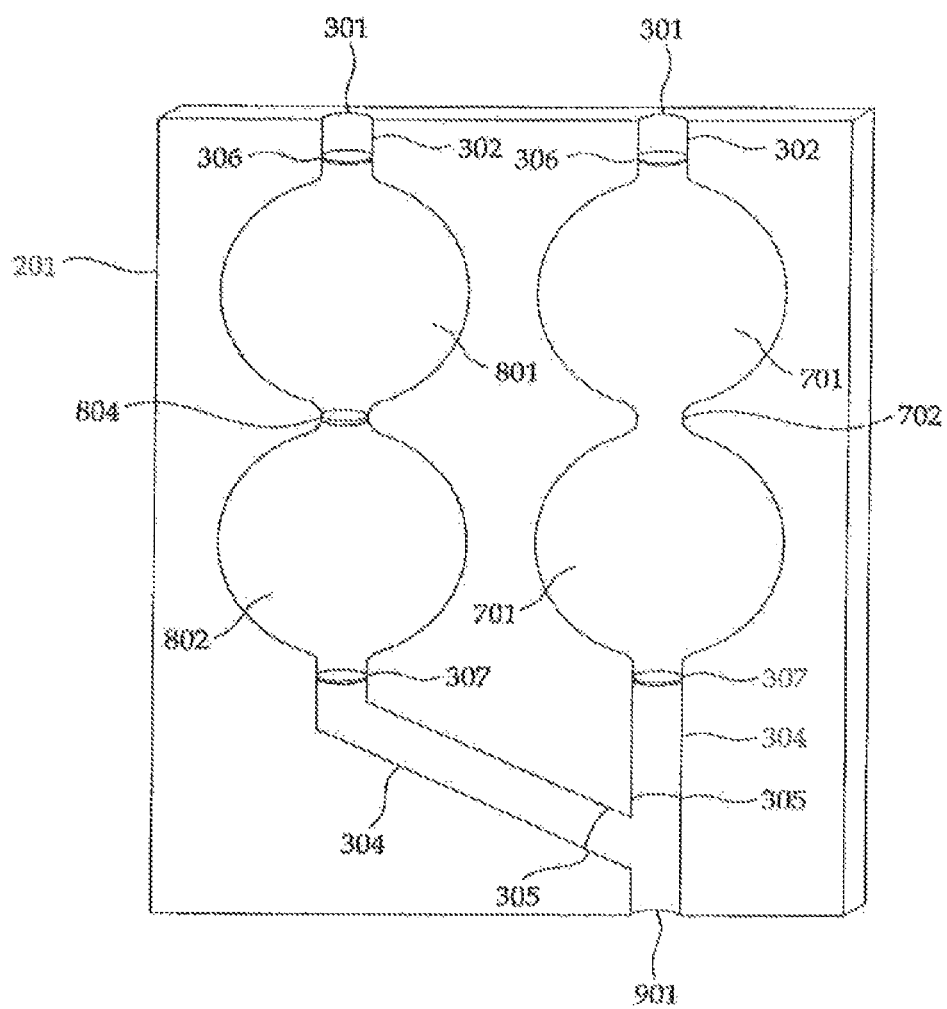
FIGS. 10A and 10B illustrate two preparation unit configurations, according to certain embodiments of the disclosure.
Figure 10B:
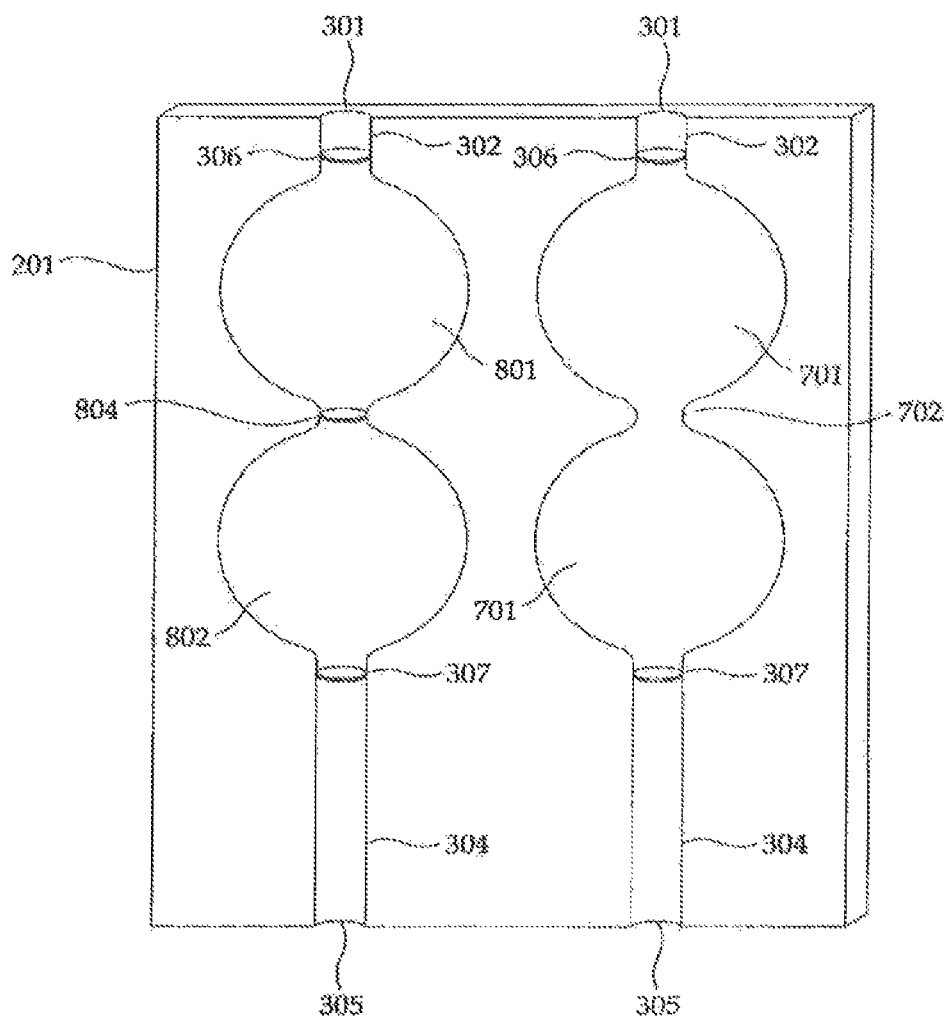

FIGS. 10A and 10B illustrate two preparation unit configurations, according to certain embodiments of the disclosure. One of the preparation units, as shown in both FIG. 10A and FIG. 10B, comprises a single reservoir containing two interconnected compartments 701. Such a preparation unit has been described above with reference to FIG. 8. The other preparation unit shown in both FIG. 10A and FIG. 10B comprises two reservoirs 801 and 802 connected by a channel 803 and sealed by a seal 804. Such a preparation unit has been described above with reference to FIG. 9. Each preparation unit has a respective first opening 301 and a respective second opening 305. The first openings of both preparation units may constitute the first openings of the cartridge.

The two configurations of the cartridge, depicted by FIGS. 10A and 10B, differ relative to the second opening provided as an outlet to the combination of preparation units. For example, in one embodiment, the cartridge depicted at FIG. 10A may include a single cartridge second opening 901 which is in fluid communication with the second openings 305 of the respective preparation units. In another embodiment, the cartridge depicted by FIG. 10B may include a second opening 305 associated with each preparation unit, where each of the second openings 305 also constitute outlets of the preparation compartment 201.

In the described embodiments, each preparation unit of a cartridge may be configured for receiving of a sample fluid from a respective carrier. In other embodiments, however, a single carrier may be structured such that the single carrier may introduce a sample fluid into a plurality of preparation units of a cartridge. The sample fluid may be introduced into the preparation units of a cartridge simultaneously or at different times.

The output fluid of each preparation unit may flow into the analyzing compartment at different times. Further, the output fluid of each preparation unit may be subjected to separate analysis processes.

Embodiments including two parallel preparation units may enable performance of two separate independent procedures relative to the sample fluid. For example, in certain embodiments, the cartridge may be configured for performing a complete blood count. In such embodiments, the cartridge may comprise two parallel preparation units, where one preparation unit is configured for preparation of red blood cells for analysis, and the other preparation unit is configured for preparation of white blood cells for analysis.

Although the cartridges depicted by FIGS. 10A and 10B comprise two preparation units, other configurations may also be used depending on the requirements of a particular application. The number of preparation units included in a cartridge, as well as the number of reservoirs included in each preparation unit, and the number of reservoirs containing more than one compartment may differ, as the configuration of a cartridge may be tailored for performance of desired procedures and/or for purpose of preparing the sample fluid for certain analysis procedures.

Figure 11:
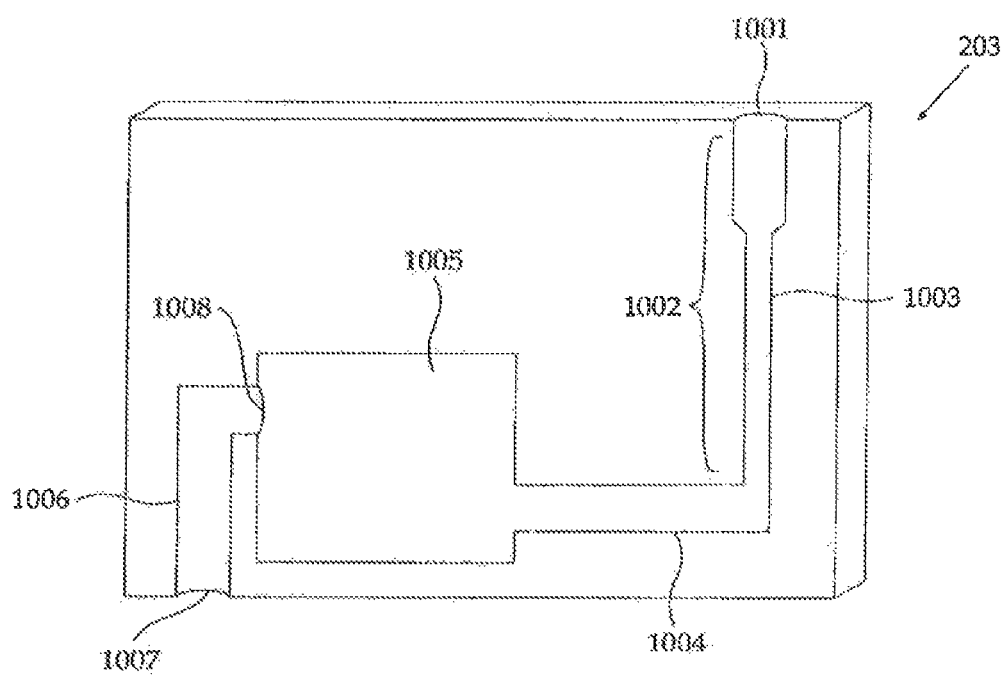
FIG. 11 diagrammatically illustrates an analyzing compartment, according to exemplary disclosed embodiments.

FIG. 11 diagrammatically illustrates an analyzing compartment 203, according to certain embodiments of the disclosure. The analyzing compartment 203 may include an analysis vessel 1002, configured for receiving the output fluid conveyed by a preparation unit or units and for presenting the output fluid in a manner that allows analysis of the output fluid. A third channel 1004 may be coupled to the analysis vessel 1002 and may be configured for emptying disposable output fluid therefrom. In some embodiments, the analysis vessel and the third channel together may comprise an analyzing unit. A waste container 1005 configured for storing disposed output fluid may be coupled to the analysis unit via the third channel 1004. The waste container 1005 may also be coupled to a vacuum pump, such as vacuum pump 104 via a fourth channel 1006 and opening 1007.

An output fluid may flow from a preparation unit into the analyzing unit 203 via a third opening 1001. Inside the analysis vessel 1002, the output fluid may be presented to an analyzing system 101. After being subjected to analysis, the output fluid may be disposed via the third channel 1004 into the waste container 1005 and stored therein.

The flow of the output fluid inside the analyzing unit may be driven by a suction force generated by the vacuum pump 104, which may be included as part of the analyzing system 101. The vacuum pump may be coupleable to the analyzing unit through opening 1007, fourth channel 1006, opening 1008, and waste container 1005. Although the suction force may be applied to the waste container 1005, the stored output fluid may not flow out therefrom. Instead, the waste container may be designed as a liquid trap. Opening 1008 may be located above the level of the stored output fluid in container 1005 in order to provide a liquid trap.

In some embodiments, analysis vessel 1002 may a micro channel 1003 configured to align cells contained in the output fluid into a pattern facilitating analysis. For example, in some embodiments, micro channel 1003 may align flowing cells in the output fluid into a single plane, which may facilitate acquisition of images of the flowing cells by a camera 107. In other embodiments, such cells may be probed by a focused light beam/laser beam, in a cytometer for example. The aligning of the cells may be performed by a method known as viscoelastic focusing. Viscoelastic focusing is described in PCT Publication No. WO2008/149365 entitled "Systems and Methods for Focusing Particles", While a microchannel configured for viscoelastic focusing is further described in PCT Publication WO2010/013238, entitled "Microfluidic System and Method for Manufacturing the Same", both of which are incorporated herein by reference. The aligned cells may then be optically analyzed, through a transparent or translucent surface (e.g., viewing area) of the microchannel 1003.

Figure 12:
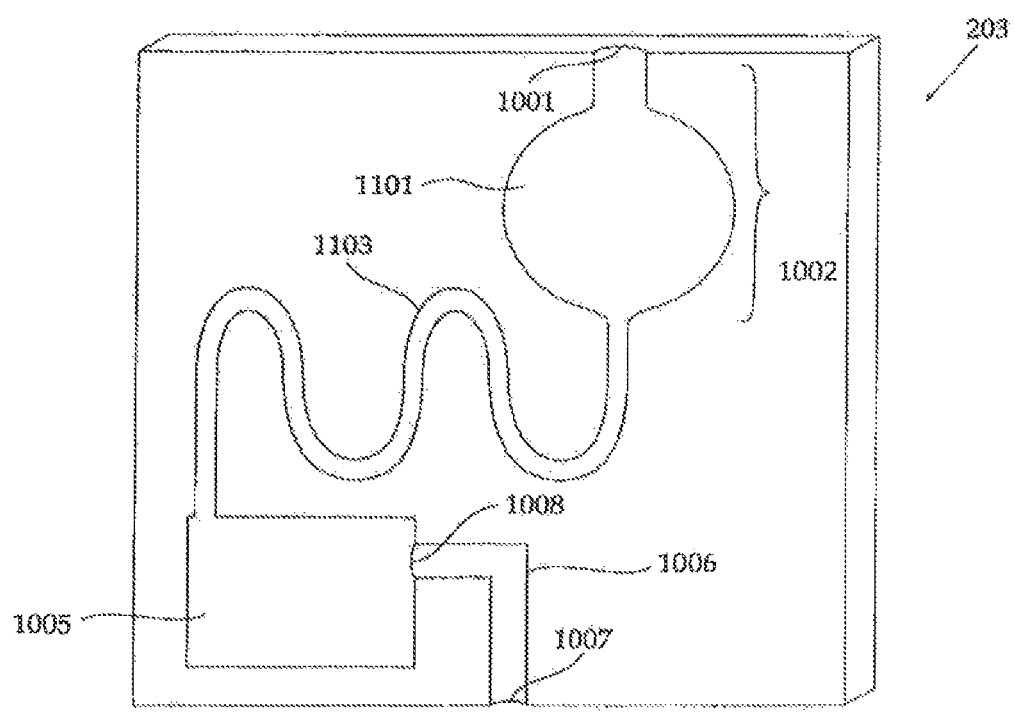
FIG. 12 diagrammatically illustrates an analyzing compartment, according to exemplary disclosed embodiments.

FIG. 12 illustrates another analyzing compartment 203, according to certain embodiments of the disclosure. The analyzing compartment 203 of FIG. 12 may be configured for determination of blood hemoglobin level. This compartment may include an analysis vessel 1002 which may include an analyzing reservoir 1101 coupled to a third channel 1103. Channel 1103 may include a small cross section and a long length relative to analyzing reservoir 1101, for example.

The analyzing reservoir 1101 may contain a powdered oxidizing agent and/or a lysing agent. The agent may be Sodium Dodecyl Sulfate (SDS), TritonX or another suitable oxidizing/lysing agent. When the reservoir 1101 is filled with the output fluid, which may include a derivative of a blood sample, the oxidizing agent may be dissolved. The dissolved oxidizing agent lyses the red blood cells of the derivative of the blood sample, which may lead to release of hemoglobin. The released hemoglobin may then be oxidized by the oxidizing agent to form methemoglobin (Which is a form of hemoglobin which cannot release bound oxygen). Concentration of methemoglobin may then be determined using a spectrometer, by measuring an absorption of one or more wavelengths. Thus, in some embodiments, the fluid analyzer 22 in such an embodiment may include a spectrometer.

According to certain embodiments, a powdered agent may freely reside inside reservoir 1101. Alternatively, the powdered agent may coat the inner surface of the reservoir 1101. To enlarge the contact area between the agent and the derivative of the blood sample, according to certain embodiments, the inner surface of the reservoir may contain projections such as pillars, baffles, or other structures, coated with the agent. Alternatively or additionally, a powdered oxidizing agent may be attached to a carrier, such as sponge, that resides in (e.g., fills) the reservoir. In addition to powdered agents, other agents, such as gels, for example, may be used.

Hemoglobin oxidation and absorption measurements may require a certain amount of time for each. Accordingly, the derivative of the blood sample may be retained inside the analyzing reservoir for a suitable period of time. In some embodiments, it may be possible to achieve retention of the sample fluid in the analyzing reservoir by applying resistance to the flow, hence slowing it down. One way for applying such resistance may be by means of a long third channel 1003 having a small cross section coupled to the analyzing reservoir 1101. When the channel is empty, no resistance or a low resistance to flow may be provided. Under such conditions, the derivative of the blood sample may flow freely into the analysis vessel 1002 and the analyzing reservoir 1101 via the third opening 1001. However, filling the third channel with a derivative of the blood sample may cause the resistance to increase, which may slow or halt flow in the analyzing reservoir 1101.

Figure 13:
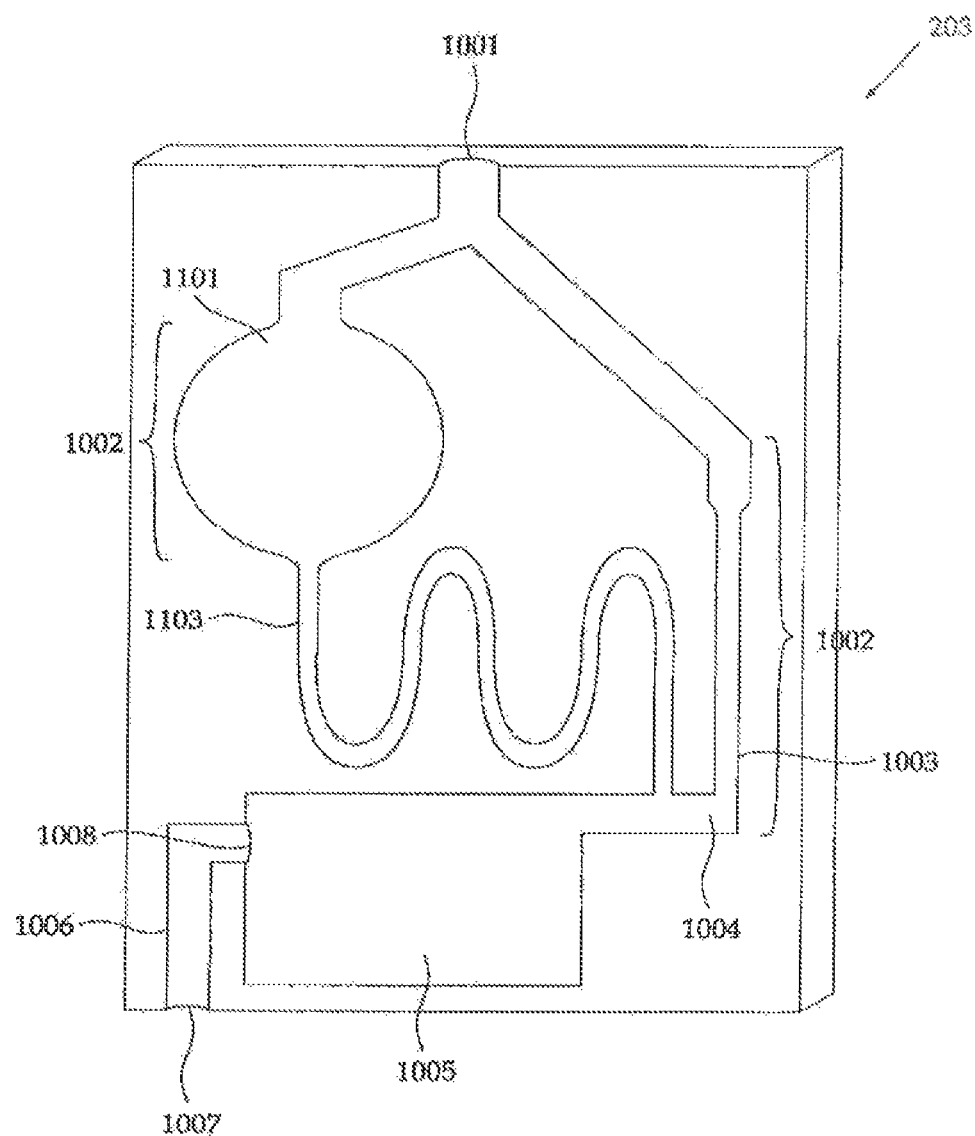
FIG. 13 diagrammatically illustrates an analyzing compartment, according to exemplary disclosed embodiments.

FIG. 13 diagrammatically illustrates an analyzing compartment 203, comprising two analyzing units, according to certain embodiments of the disclosure. One of the analytical units comprises a microchannel 1003, similar to the analyzing unit depicted in FIG. 11. The other analyzing unit comprises an analyzing reservoir 1101, similar to the analyzing unit depicted in FIG. 12. In some embodiments, the two analyzing units may be coupled on one side to a third opening 1001 for purposes of obtaining the output fluid from one or more preparation units. On the other side the analyzing units may be coupled to the waste container 1005, wherein disposable fluid may be disposed. In some embodiments, the two analyzing units may be configured in parallel, as shown in FIG. 13.

It is noted that such parallel arranged analyzing units within an analyzing compartment may enable performance in parallel of two separate types of analysis of the output fluid. For example, using the analytical compartment depicted by FIG. 13, cell counting and measuring of hemoglobin level of a derivative of a blood sample may be performed. The two types of analysis may be performed using different analyzing modules included in fluid analyzer 22 (e.g., a camera, a spectrometer, etc.).

Figure 14A:
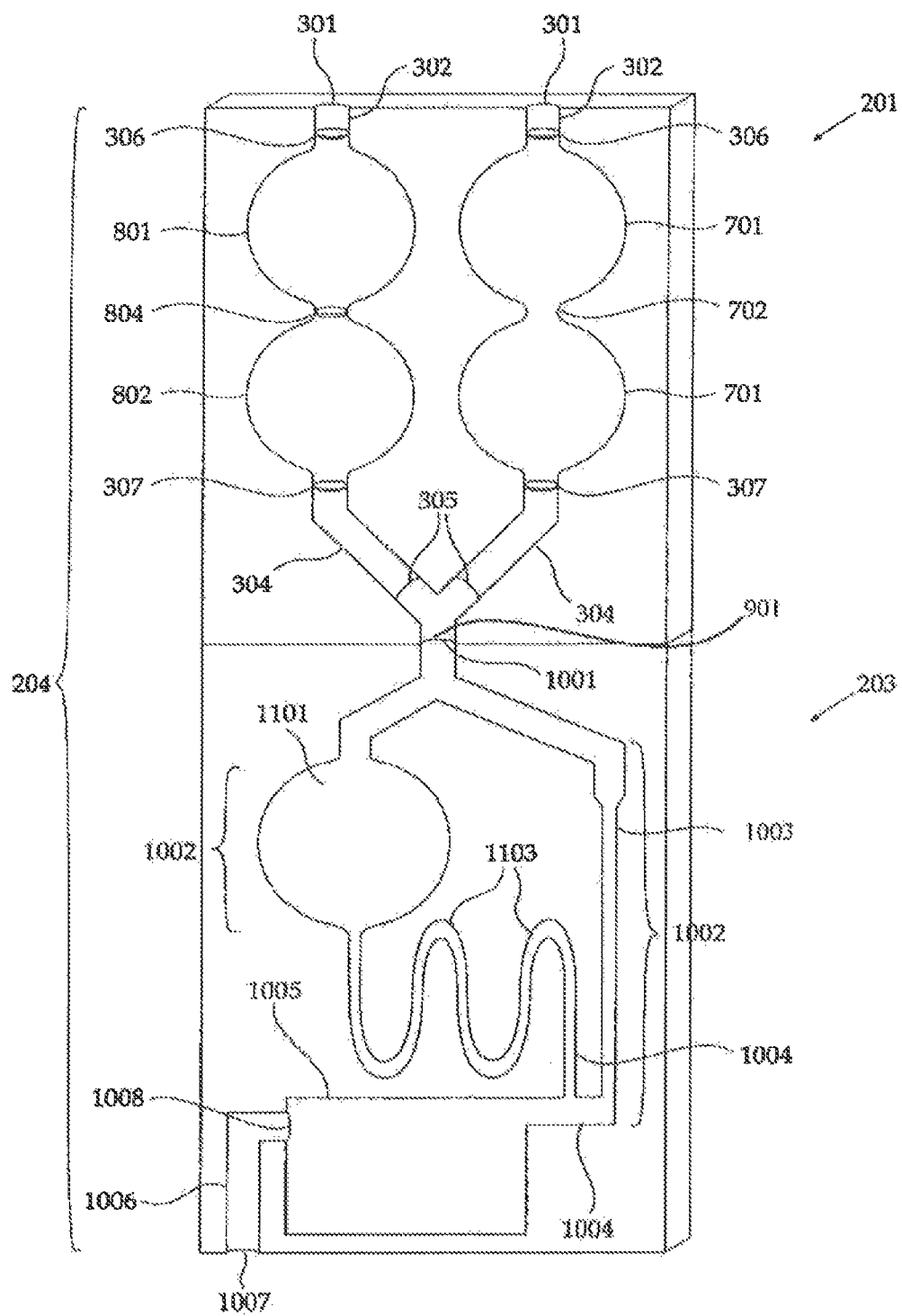
FIGS. 14A and 14B show a cartridge comprising a preparation compartment and an analyzing compartment, according to exemplary disclosed embodiments.
Figure 14B:
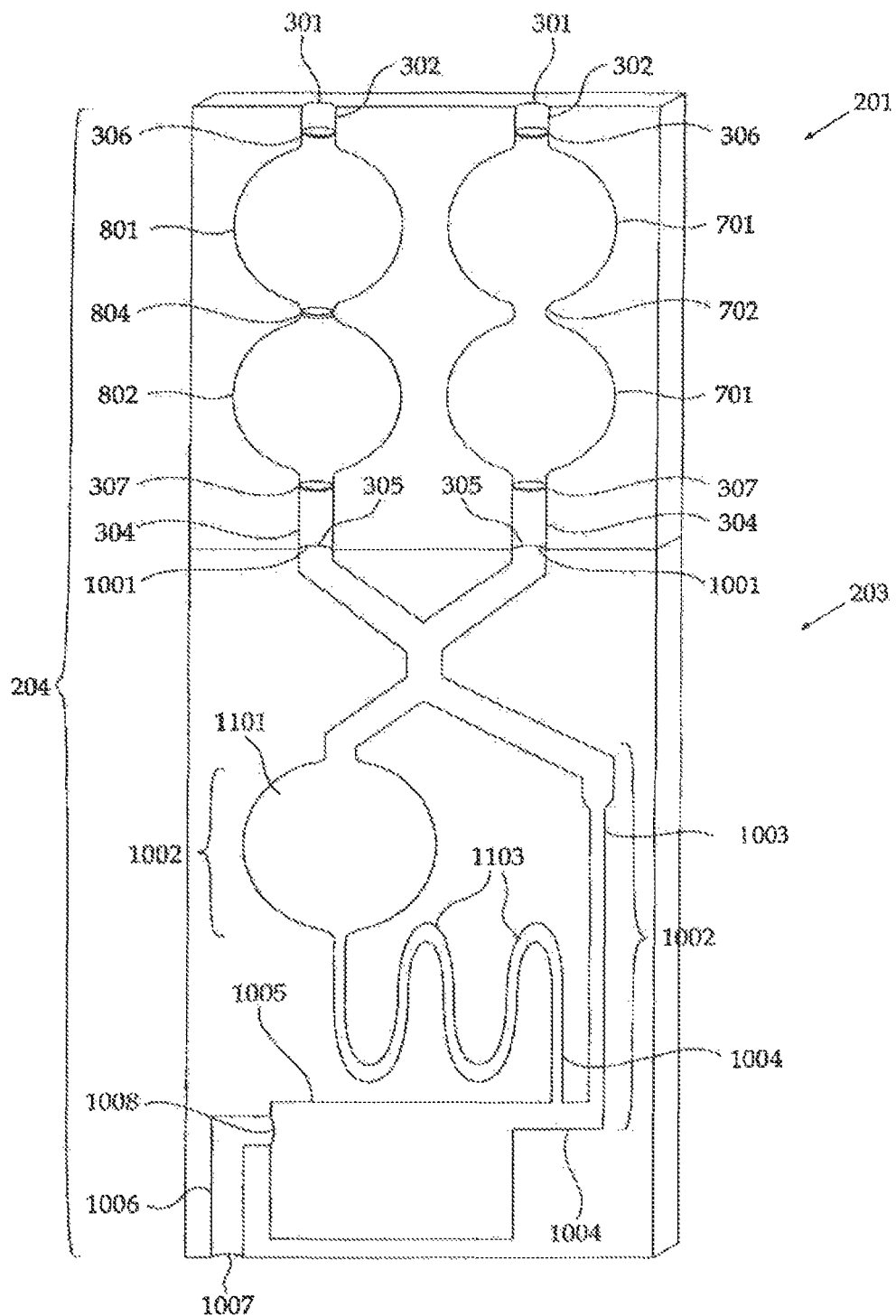

FIGS. 14A and 14B show a cartridge comprising a preparation compartment 201 and an analyzing compartment 203, according to certain embodiments of the disclosure. Preparation compartment 201 of the cartridge 204 has been described above, with reference to FIGS. 10A and 10B. In the example presented in FIGS. 14A and 14B, the preparation compartment may include two preparation units, the first unit and the second unit. The first preparation unit, which may include a single reservoir containing two interconnected compartments 701, has been described above relative to FIG. 8. The second preparation unit, comprising two reservoirs 801 and 802, has been described in detail above, with reference to FIG. 9.

The analyzing compartment 203 of FIGS. 14A and 14B may contain two analyzing units. One of the analyzing units, comprising a microchannel 1003, may be configured to align cells contained in the output fluid into a single plane allowing taking images of the flowing cells using a camera, or probed by a focused light beam/laser beam as done in a cytometer. The other analyzing unit, comprising an analyzing reservoir 1101 coupled to a long small cross-sectioned third channel 1004, may be configured for determination of hemoglobin level, e.g., using a spectrometer.

To allow flow of the output fluid prepared for analysis from the preparation compartment 201 to the analysis compartment 203, the two compartments may be interconnected by means of the opening 901 of the preparation compartment coupled to opening 1001 of the analyzing compartment.

According to certain embodiments, cartridge 204 may be configured to receive a blood sample and may enable performance of a blood count. A blood count performed by the cartridge 204 may include determination of number of red blood cells, white blood cells (total count) and platelets present in the sample, as well as determination of number of each of the white blood cell types (differential count). The white blood cell types may be neutrophils, lymphocytes, monocytes, eosinophils and monocytes or part thereof. Additional types and sub-types of white blood cells may also be counted. Furthermore, the disclosed embodiments may be applicable to any type of cells circulating in the blood, including, e.g., circulating tumor cells, platelets aggregates and others.

In the described embodiments, cell counting may be performed by means of acquiring images of flowing cells by a camera or by probing by a focused light beam/laser beam as done in a cytometer. In order to allow reliable counting, the cells may be brought into a focal place of the analyzing optics. Hence, the cells should be aligned in a single plane, e.g., by viscoelastic focusing. The method is based on suspending cells in a focusing medium of certain viscoelastic properties causing the cells suspended therein to align into a single plane if being flowed in a microchannel of a certain geometry (e.g., having a length of greater than 100 microns and at least one cross-sectional dimension less than 100 microns, e.g., between 5 microns and 100 microns). Preparation of a sample fluid for counting, performed in preparation compartment 201 of a cartridge 204, may include adding focusing media to the sample fluid, thus yielding a derivative of the sample fluid.

The first preparation unit may be configured for preparing a blood sample for determination of number of red blood cells, white blood cells (total count) and platelets present therewithin. A substance contained in reservoir 701 comprises focusing medium with added surfactants. The focusing medium may include a buffer containing, for example, soluble high molecular weight polymers. The buffer may include any isotonic buffer suitable for managing living cells, including, for example, Phosphate Buffered Saline (PBS). Examples of soluble polymers suitable for providing the blood sample with viscoelastic properties include polyacrylamide (PAA), polyethylene glycol (PEG), Propylene Glycol, etc. The surfactants added to a focusing media may act as sphering agents that may cause the shape of red blood cells to change from biconcave discs into spheres, which may facilitate acquisition of higher quality images of the cells. Examples of surfactants include SDS (Sodium Dodecyl Sylphate) and DDAPS (dodecyldimethylammoniopropanesulfonate). The composition of the focusing medium is disclosed, e.g., in PCT Publication No. WO2008/149365 entitled "Systems and Methods for Focusing Particles", incorporated herein by reference.

The procedure performed by reservoir 701 may include mixing of the delivered blood sample with a focusing medium. After mixing has been completed, the succeeding seal 307 may be breached by pressure, allowing the generated output fluid to flow into the analytical compartment 203.

The second preparation unit may be configured for preparing a blood sample for differential count of white blood cell types. In certain embodiments, the preparation may include chemical staining of cells, where two consecutive staining procedures may be performed in reservoirs 801 and 802 of the preparation unit.

The substance contained in reservoir 801 may comprise cell staining reagents dissolved in a focusing medium. Examples of cell staining reagents include Phloxine B, Biebrich Scarlet and Basic Orange 21. As a fixation of cells may be needed in some cases, fixating reagents, including, for example, formaldehyde or formalin, may also be included. Following mixing of the blood sample with the substance, an incubation may be performed, allowing staining. Upon expiration of a predetermined incubation time, a seal 804 separating reservoir 801 from reservoir 802 may be breached by pressure, resulting in release of the generated output fluid towards the reservoir 802.

The substance contained in reservoir 802 may comprise other cell staining reagents dissolved in a focusing medium. Examples of cell staining reagents included in reservoir 802 may include Methyl Green, Methylene Blue and Barrel's Blue. Following mixing of an input fluid (which constitutes the output fluid of reservoir 801) with a substance, a second incubation may be performed, allowing the second staining process to occur. Upon expiration of a second predetermined incubation time the seal 307 of the second preparation unit may be breached by pressure allowing the generated output fluid to flow into the analytical compartment 203.

In some embodiments, preparation of cells for analysis may include immuno-based staining of the cells. In these embodiments, one or both reservoirs of a preparation unit may contain reagents suitable for immune-staining, where the reagents and the focusing medium may be contained within a single reservoir or in different reservoirs. Examples of reagents suitable for immune-staining include antibody-coated micro beads of different colors, such as CD14/CD15 and a combination of stains.

The output fluids flowing out of the second openings 305 of both preparation units may be conveyed to a single channel that is coupled to the analysis vessels of both analyzing units. Analysis of the output fluids may be performed sequentially or simultaneously. The sequential analysis may be enabled by temporally separating flows of the two output fluids, a separation that may be controlled in the preparation compartment. As described above, the preparation process performed by a first preparation unit may include mixing in a single reservoir without incubation, while the preparation process performed by a second preparation unit may include, in addition to mixing in two different reservoirs, two staining procedures that may require incubation time. Hence, the output fluid of the first preparation unit may be ready to flow into the analyzing compartment before the output fluid of the second preparation unit is ready to flow into the analyzing compartment.

Upon flowing into the analyzing compartment 203, the output fluid of the first preparation unit may be divided between the two illustrated analyzing units. Part of the fluid may enter the microchannel 1003, wherein the cells within the output fluid may become aligned into a single plane via viscoelastic focusing, for example. The aligned cells may then be optically analyzed, through a transparent or translucent surface or window associated with microchannel 1003. The output fluid then flows into waste container 1005, wherein it may be stored. The other part of the output fluid may enter the analyzing reservoir 1101, wherein the cells within the output fluid become lyzed and their hemoglobin content quantified in a way described with reference to FIG. 12.

The flow of the output fluid of the first preparation unit into the analyzing compartment may be aborted prior to breaching the seal 307 of the second preparation unit in order to minimize or prevent mixing of the output fluids, which could hinder the analysis. This is enabled due the second channel 304 of the first preparation unit being re-sealable. The re-sealing of the channel may be performed, for example, by pressure applied to the succeeding seal or to another area of the second channel 304 of the first preparation unit.

As described above, the length and cross-sectional shape of the third channel 1103 coupled to reservoir 1101, may provide resistance to flow at the reservoir, especially under certain conditions. Hence, upon breaching seal 307 of the second preparation unit, substantially all the output fluid may flow into the analyzing compartment 203 and may be conveyed to the microchannel 1003 instead of being split between the two analysis units, inside the microchannel 1003, the cells within the output fluid of the second preparation unit may become aligned into a single plane hence allowing optical analysis. The output fluid may then flows into the waste container 1005, wherein it is stored.

Figure 15A:
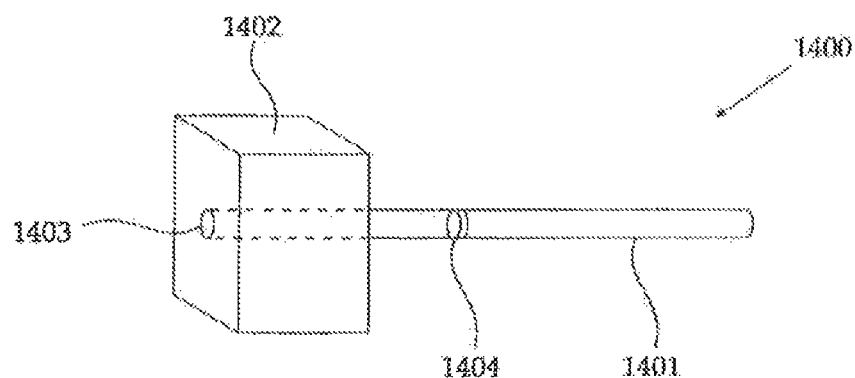
FIGS. 15A, 15B and 15C, diagrammatically depict samplers, according to presently described embodiments.
Figure 15B:
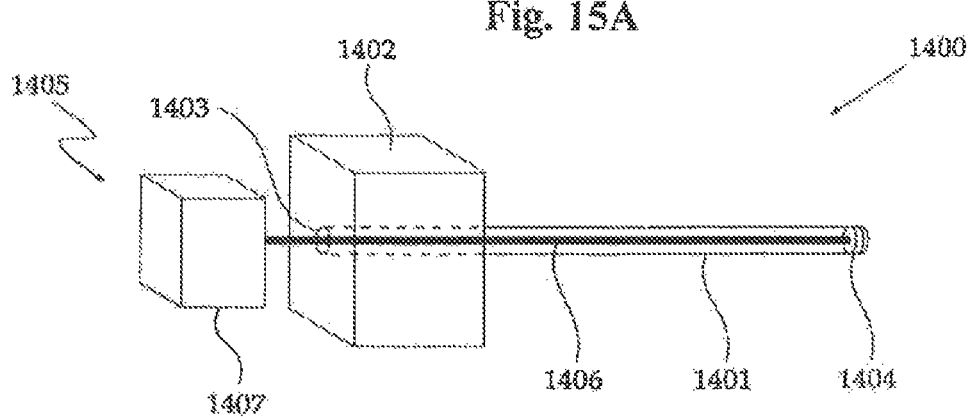
Figure 15C:
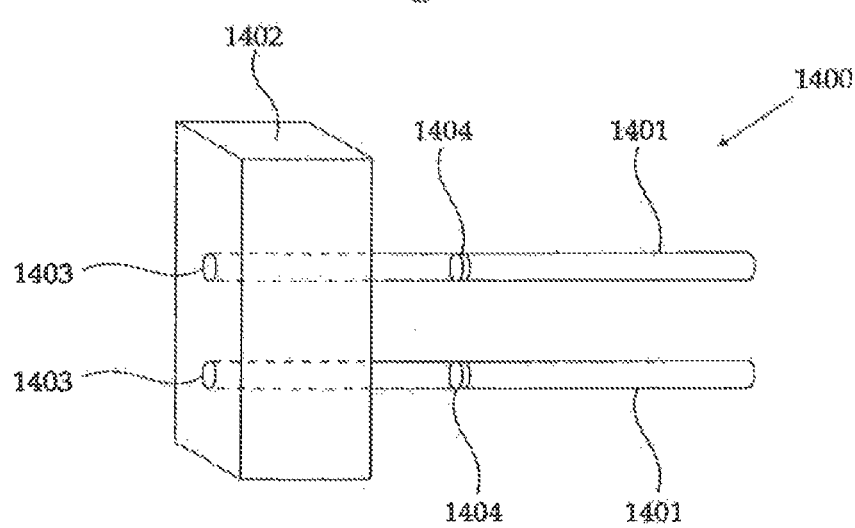

FIGS. 15A, 15B and 15C, diagrammatically depict samplers, according to the presently described embodiments. A sampler 1400 may be configured to sample fluid and to introduce it into the cartridge 204, e.g., in precise amounts. The sampler depicted by FIG. 15A may include a carrier 1401 attached to a handle 1402. In some embodiments, the carrier may include a capillary. Inside the capillary, a seal/plug may be formed, and the seal or plug may include any type of material or configuration that allows at least some air to flow, but blocks liquid flow. For example, in some embodiments a hydrophobic membrane 1404 may be affixed at a pre-determined distance from the capillary outlet. The capillary 1401 may include any type of capillary with a hydrophobic membrane affixed inside and suitable for a particular application. For example, capillaries manufactured by DRUMMOND Aqua-Cap™ Microdispenser may be used in the presently disclosed embodiments.

Fluid sampling may be performed by immersing the outlet of the capillary 1401 in the fluid. The sample fluid may be driven into the capillary by capillary force. The hydrophobic membrane 1404 affixed inside the capillary 1401 may facilitate the process, as it allows the air displaced by the sample fluid to flow out. The fluid fills the capillary until reaching the hydrophobic membrane. It should be appreciated that due to the hydrophobic nature of membrane 1404, the fluid does not come into contact with the membrane. Therefore, there may he no sample fluid absorbance in the membrane, or in other words, no loss of fluid volume occurs to the membrane. Thus, the final volume of a sampled fluid may be determined based on a distance of the hydrophobic membrane 1404 from the capillary outlet and by the capillary's inner diameter.

Once the fluid has been sampled, it may be delivered or introduced into the cartridge 204 by inserting the capillary 1401 through the first opening 301 thereof. At this stage only a limited leakage of a sample fluid from the capillary into a reservoir 303 may occur, as the fluid may be held inside by capillary forces. A plunger 1405 may be used to push the sample fluid out of the capillary into the reservoir 303. The plunger 1405, depicted in FIG. 15B may include a plunging member 1406 attached to a holding member 1407. The plunging member 1406 may be configured for insertion into the capillary 1401 through a capillary inlet 1403 located in the handle 1402. The plunger pushes the hydrophobic membrane 1404 until it reaches the capillary outlet, optionally resulting in the delivery of the entire sample fluid into the reservoir 303. It should be considered though that if the plunging member 1406 is not long enough for reaching the capillary outlet, a certain dose of fluid may remain in the capillary. Hence the volume of the sample fluid delivered into the reservoir may depend on a length of plunging member 1406 relative to a length of capillary 1401. The capillary's diameter may be known in advance along with the length of the capillary and the length of the plunger. Hence, the volume of the fluid transferrable by the sampler can be predetermined.

Sampling and plunging as described above may enable delivery into the reservoir of a fixed volume of sample fluid. The ability to deliver a fixed volume of a fluid may be important, as deviations in the delivered volume from sample to sample may affect the reliability of the sequential analysis. There may be no need to flush the blood out of the sampler (in this case the capillary) because the hydrophobic membrane may help to ensure that all of the sample fluid, e.g., blood, is dispensed into the first reservoir.

With reference to certain embodiments, the plunger 1405 may be included as a part of analyzing system 101, such that the plunger is inserted into the cartridge 204 upon placement thereof inside the cartridge holding unit 103 of an analyzing system 101. However, in different embodiments the plunger may constitute a separate device, whereas the insertion of a plunger into the cartridge may be performed prior to placement thereof into the cartridge holding unit 103.

As illustrated by FIG. 15C, the sampler may include two carriers 1401, wherein sampling of the fluid by the carriers is performed simultaneously or sequentially. The sampler of FIG. 15C comprising two carriers may be used, for example, for sampling and delivery of blood into a cartridge configured to allow performance of blood count. In some embodiments, the two carriers of the sampler may comprise anticoagulant-coated capillaries with a hydrophobic membrane. An anticoagulant, coating the capillaries, may serve to prevent clotting of sampled blood. An example of an anticoagulant includes EDT A (Ethylenediaminetetraacetic acid).

A fluid volume sampled by each carrier 1401 of the sampler 1400 and delivered into the cartridge 204 may be as small as 20 µl or even less. Therefore, performance of a blood count using the sampler 1400, the cartridge 204 and the analyzing system 101 may require obtaining of as little as a single drop of blood from an individual. Such a small volume of blood may be obtained by pricking the fingertip or forearm in a way performed for example by home blood glucose monitoring devices, thus sparing drawing blood from a vein, which is less convenient for patients, especially children.

Figure 16:
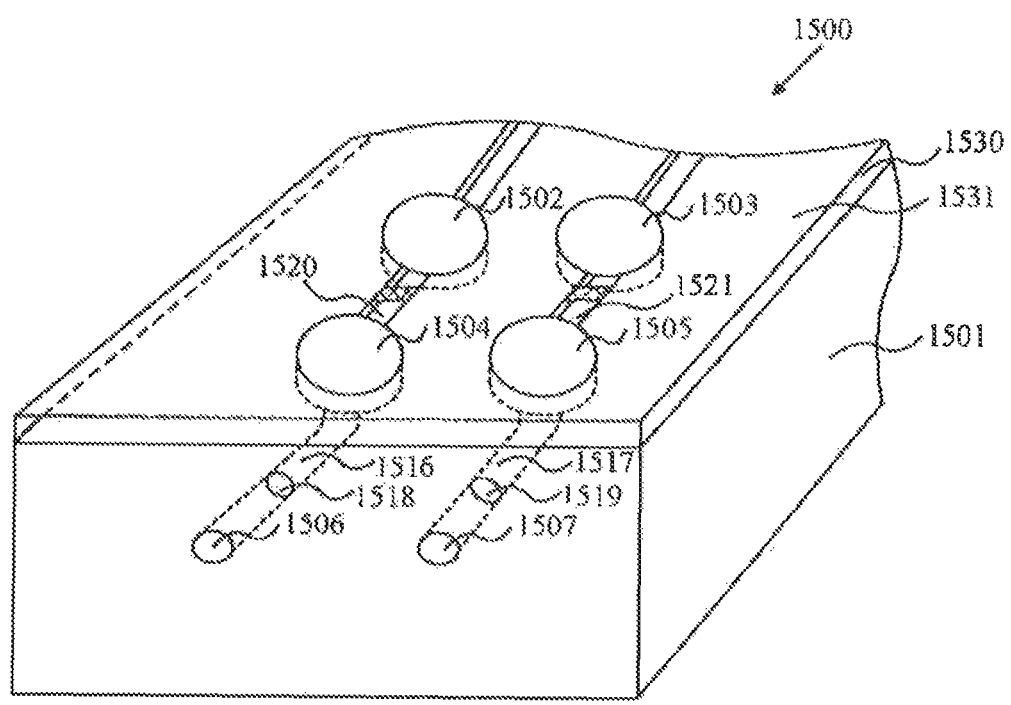
FIG. 16 shows a portion of a cartridge including a rigid frame, according to exemplary disclosed embodiments.

In some embodiments, cartridge 204 may include a substantially rigid frame at least partially housing the reservoirs of one or more preparation units. FIG. 16 shows a portion of a cartridge 1500 including rigid frame 1501. Rigid frame 1501 may comprise any rigid or semi-rigid material. For example, in some embodiments, rigid frame 1501 may be fabricated from any of PMMA, COP (Cyclic olefin copolymer), Polyethylene, polycarbonate, polypropylene, polythene, etc., or combinations thereof.

Rigid frame 1501 may be fabricated to include one or more structures associated with the preparation units described above. For example, in some embodiments, rigid frame 1501 may be made by injection molding and may include various flow paths, inlets, outlets, and/or reservoir elements (e.g., depressions formed in a surface of the rigid frame that provide reservoirs when covered with a cap or cover layer). Rigid frame 1501 may be provided as a substantially monolithic substrate, as shown in FIG. 15, for example. Alternatively, rigid frame 1501 may include one or more structural components associated with cartridge 204/1500 and that provide support to one or more elements of the cartridge 204/1500.

In some embodiments, rigid frame 1501 may include openings 1506 and 1507 which lead to flow channels 1516 and 1517, respectively. Opening 1506 and/or opening 1507 may be sized to accept a sampler containing a quantity of sample fluid. For example, either or both of openings 1506 and 1507 may be sized to accept a capillary 1401 associated with sampler 1400. In some embodiments, a spacing between openings 1506 and 1507 may be provided to match a spacing between capillaries 1401 provided on a dual capillary sampler, as shown in FIG. 14C.

Further channel 1516 and/or 1517 formed in the rigid frame or otherwise associated with the rigid frame may be configured to align and stabilize a capillary tube of a sampler. Such a configuration may facilitate alignment and insertion of a capillary 1401 into cartridge 1500. Further, these channels may help guide the capillary tubes to a desired location within the rigid frame or cartridge 204 and may protect the capillary tubes from breaking while inserted into rigid frame 1501.

In some embodiments, openings 1506 and 1507 and channels 1516 and 1517 may provide fluid flow paths to one or more reservoirs associated with cartridge 1500. For example, as shown in FIG. 15, channel 1516 may lead to reservoir 1504, and channel 1517 may lead to reservoir 1505. Thus, sample fluid provided to channel 1516 may flow to reservoir 1504, and sample fluid provided to channel 1517 may flow to reservoir 1505. It should be understood that although FIG. 15 shows two openings in the substantially rigid frame, the substantially rigid frame may include any number of openings without departing from the scope of the present disclosure. One or more of the openings in the substantially rigid frame may be configured to align and stabilize a capillary tube.

Reservoirs 1504 and 1505 may be included as part of preparation units (as described above) of cartridge 1500. For example, reservoir 1504 may be coupled to another reservoir 1502 via a channel 1520 and a seal 1507. Similarly, reservoir 1505 may be coupled to another reservoir 1503 via a channel 1521 and a seal 1508.

In some embodiments, cartridge 1500 and its associated preparation units may be formed based upon a two-part construction. For example, a first part of the cartridge 1500 may include rigid frame 1501, including molded components for providing at least a part of the structures associated with the preparation units of cartridge 1500. A second part of the cartridge may include a film 1530 disposed on the rigid frame 1501. Disposing film 1530 upon rigid frame 1501 may complete at least a portion of the structures or components of the preparation units. For example, reservoir 1504 (and the other reservoirs shown in FIG. 15) may include a first portion comprising a depression formed in rigid frame 1501. When film 1530 is placed over rigid frame, a portion of the film will cover the depression associated with reservoir 1504. Further, forming film 1530 from an elastic material may also enable one or more of the reservoirs associated with cartridge 1500 to he pressable, as described above.

Film 1530 may be formed from any suitable material. In some embodiments, film 1530 may be formed from PVC, Polypropylene, polyethylene, polyurethane and laminates containing aluminum and PE, or combinations thereof.

In some embodiments, one or more of the rigid frame 1501 and the film 1530 may be formed of materials that may bond together when exposed to heat. During construction of the two-part structure of cartridge 1500, as shown in FIG. 15, varying levels of heat may be applied to achieve desired results. For example, where high temperatures (e.g., 140C-180C) are applied, film 1530 may be caused to permanently weld to the material of rigid frame 1501. In other areas, where little or no heat is applied, film 1530 may remain unbonded to the underlying rigid frame. And, in areas where heat is provided at a level below a welding threshold for the materials (e.g., 100C-130C), the material of film 1530 may bond together with the material of rigid frame 1501, but the bond may be non-permanent. That is, in these areas, the bonded materials may be later pulled apart from one another. In some embodiments, the selective bonding described above may be achieved, for example, using a film 1530 having a multi-layer structure. A first sub-film of the multi-layer structure (e.g., the lowest layer that first contacts rigid frame 1501) may include a material that forms a relatively weak bond with the material of rigid frame 1501. Thus, subsequent force on an area where the first sub-film has been bonded to rigid frame 1501 may result in separation (e.g., peeling) of the sub-film and, therefore, the entire film 1530 away from rigid frame 1501.

In some embodiments, a multi-layer structure of film 1530 may include a second sub-film disposed above the first sub-film. The second sub-film may form a more permanent bond with the material of rigid frame 1501 through the application of a higher temperature. For example, in some embodiments, the higher temperature may cause the first sub-film to melt and flow away from the bonding area, which may enable the second sub-film to bond directly to the rigid frame material (either permanently or semi-permanently).

This type of bonding may facilitate construction of components associated with the preparation units of cartridge 1500. For example, in areas such as region 1531 away from the structures of the preparation units, a high temperature may be applied to permanently weld the material of film 1530 to rigid frame 1501. In areas associated with reservoirs 1502, 1503, 1504, 1505 and associated with channels 1520 and 1521, heat application may be avoided such that film 1530 remains free of rigid frame 1501 in these regions. In regions associated with seals 1507 and 1508 a sub-welding heating level may be used such that film 1530 is tacked or temporarily bonded to rigid frame 1501. These seals may be referred to as "peel seals," as pressure placed on the seal, for example by a fluid within reservoir 1504 pressing on seal 1507, may cause film 1530 to peel away from frame 1501. Under such circumstances, fluid may be allowed to flow through the seal. While these peel seals may be frangible, fluid flow through a broken seal 1507 or 1508 may be halted by, for example, applying pressure to film 1530 in the regions of the seals in order to close the fluid pathway at the seals.

Cartridge 1500 may also include seals 1518 and 1519 disposed within channels 1516 and 1517, respectively. Seals 1518 and 1519 may prevent fluids or other materials preloaded into reservoirs 1504 and 1505, for example, from escaping from the cartridge or from becoming contaminated from the surrounding environment.

Figure 17A:
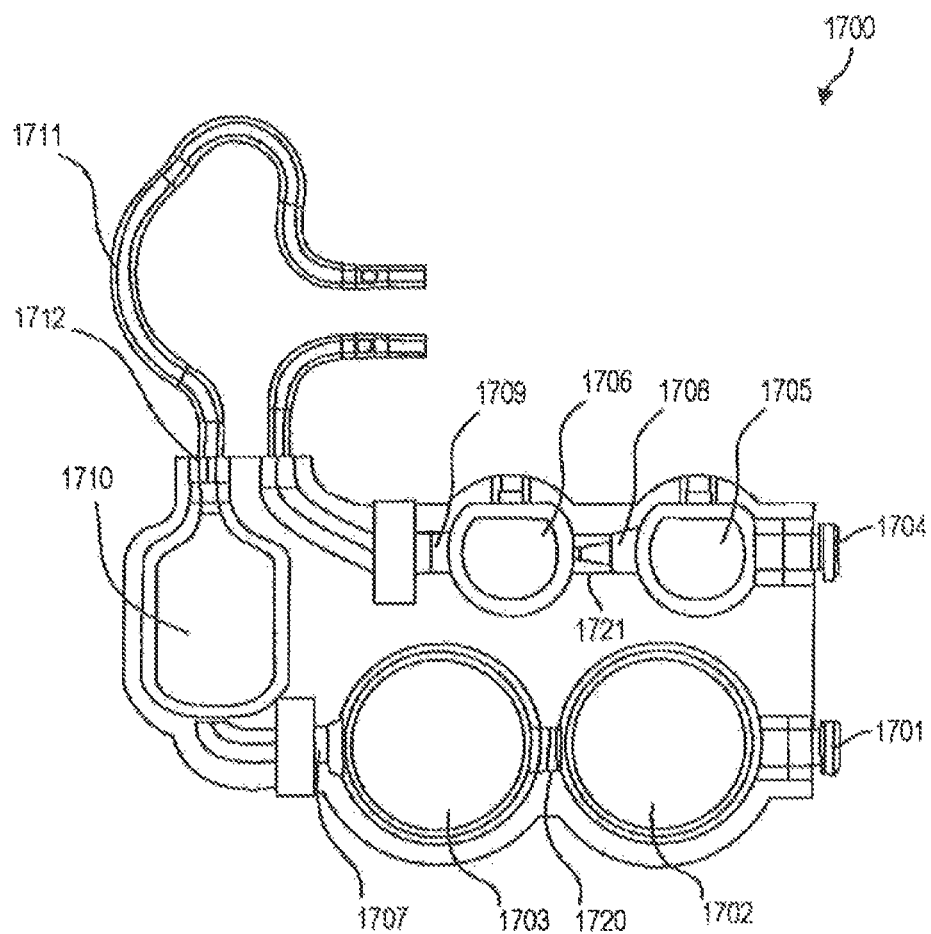
FIG. 17A illustrates a cartridge, according to an exemplary disclosed embodiment.

FIG. 17A illustrates a cartridge 1700, according to an exemplary disclosed embodiment. As shown in FIG. 17, the cartridge 1700 includes a first inlet or opening 1701, a first reservoir 1702, a second reservoir 103, a second inlet or opening 1704, a third reservoir 1705, and a fourth reservoir 1706. Inlet 1701 is associated with the first reservoir 1702, and inlet 1704 is associated with the third reservoir 1705. The example cartridge further includes a first seal 1707, a second seal 1708, and a third seal 1709. Any or all of the seals may be fabricated as "peel seals," as described above. As shown in FIG. 17, a first flow path is formed across the first and second reservoirs 1702 and 1703, the fluid channel 1720, and the first seal 1707. A second flow path is formed across the third and fourth reservoirs 1705 and 1706, the fluid. channel 1721, the second seal 1708, and the third seal 1709.

The first flow path may be configured to mix a blood or fluid sample with a first reagent, and the second flow path may be configured to mix the blood or fluid sample with a second reagent. The reagents may be preloaded and sealed in the reservoirs. Alternatively, the reagents may be injected into the reservoirs via inlets in the cartridge. The reagents may include at least one of a white blood cell stain (e.g., acidic stain and alkaline stain), a lysing agent, a biomarker, and at least one high molecular weight polymer in fluid form. Upon the pressing of one or more of the reservoirs, the corresponding seals may be caused to open to enable any fluid in the reservoirs to flow along the respective flow path.

Cartridge 1700 may also include a buffer compartment 1710. Buffer compartment 1710 may be included within a flow path between sample fluid preparation reservoirs (e.g., reservoirs 1702 and 1703) and a fluid outlet 1712 leading to an analysis segment. in some embodiments, a tube 1711 may be provided at outlet 1712 to carry sample fluid, or derivatives thereof, to one or more analysis segments. In some embodiments, buffer compartment 1710 may remain empty of fluid prior to placing cartridge 1700 into use. Upon receiving a sample fluid into cartridge 1700 (e.g., via inlets 1701 and/or 1704), the sample fluid may be provided to a preparation unit including reservoirs 1702 and 1703 and prepared for analysis according to any of the preparation processes described above.

In some embodiments, once the sample fluid (or a derivative thereof) has been prepared and is ready for analysis, the sample fluid/sample fluid derivative may be provided to buffer compartment 1710 prior to analysis. Buffer compartment 1710 may include a reservoir and may serve as a temporary holding location within cartridge 1700 prior to analysis of the fluid. In some embodiments, fluid gathers in buffer compartment 1710 as a flow rate into buffer compartment 1710 may exceed a flow rate out of buffer compartment 1710. In other embodiments, buffer compartment 1710 may serve as a pass-through chamber for fluid where a fluid flow rate out of buffer compartment equals or, in some cases, exceeds a flow rate into buffer compartment 1710.

The amount of fluid provided to buffer compartment 1710 may be controlled by any suitable technique. In some embodiments, the prepared sample fluid from reservoirs 1702/1703 may be provided to buffer compartment 1710 by opening seal 1707 (e.g., via a super threshold pressure applied to the seal, releasing or removing a physical obstacle associated with seal 1707, or by any other opening technique) and metering into buffer compartment 1710 a desired amount of prepared fluid. One or more stepper motors may be employed, for example, to depress portions of reservoirs 1702 and/or 1703 by a predetermined amount and/or at a predetermined rate in order to provide a predetermined amount of prepared fluid to buffer compartment 1710.

Fluid provided to buffer compartment 1710 may be drawn out of buffer compartment 1710 for analysis using any suitable technique. For example, in some embodiments, a vacuum may be applied to outlet 1712 via tube 1711 in order to cause fluid to flow from buffer compartment 1710. Metering techniques (e.g., including stepper motors, plungers, flow control seals, etc.) may be used to draw out of buffer compartment 1710 a predetermined amount of fluid for analysis.

Buffer compartment 1710 may offer certain performance characteristics dependent upon the structures of a particular configuration or based upon a particular operating scheme. For example, during operation buffer compartment 1710 may function as a fluid analog to an electrical capacitor and may buffer fluid flow prior to analysis of the fluid. Buffer compartment 1710 may aid in reducing an amount of bubbles present in the fluid to be analyzed. In some embodiments, the fluid drawn from buffer compartment 1710 for analysis may be drawn from a region of buffer compartment 1710 residing below a fluid level line in buffer compartment 1710. Bubbles in the fluid provided to buffer compartment 1710, resulting, e.g., from flow of the prepared fluid through one or more components of the preparation unit, may tend to accumulate on a surface of the fluid in buffer compartment 1710. By drawing fluid from buffer compartment 1710 from below a fluid level line, such bubbies may remain in buffer compartment 1710, and the fluid drawn out of buffer compartment 1710 for analysis may be bubble free or may at least include fewer bubbles per unit volume than the totality of fluid residing in buffer compartment 1710. Further, buffer compartment 1710 may avoid complexities associated with controlling of operational characteristics of seal 1707 in order to provide a desired flow of fluid for analysis. In some embodiments, an amount of fluid provided to buffer compartment 1710 may exceed an amount of fluid.

Figure 17B:
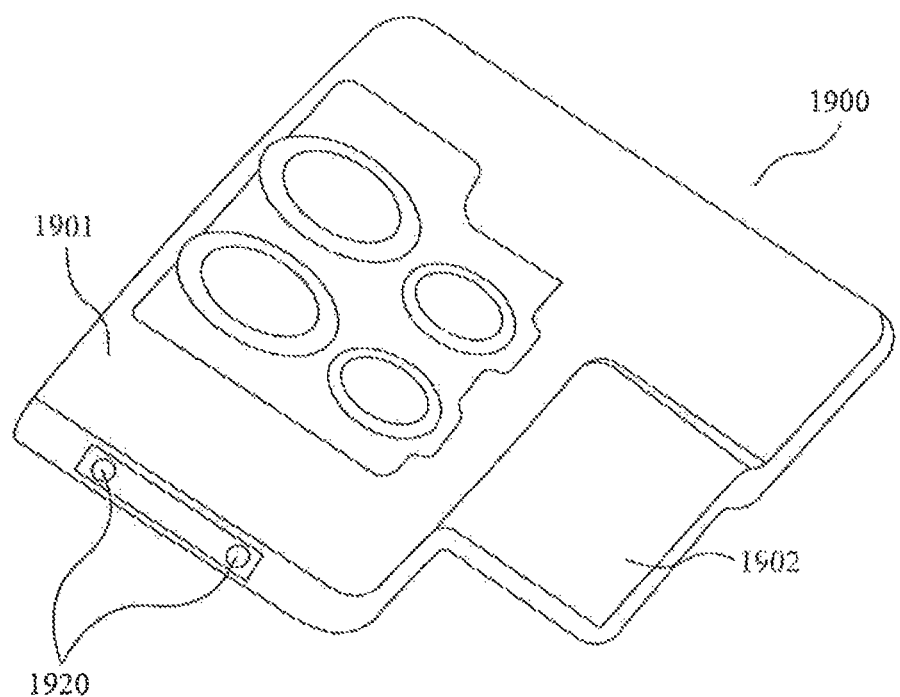
FIG. 17B illustrates a cartridge, according to an exemplary disclosed embodiment.
Figure 17C:
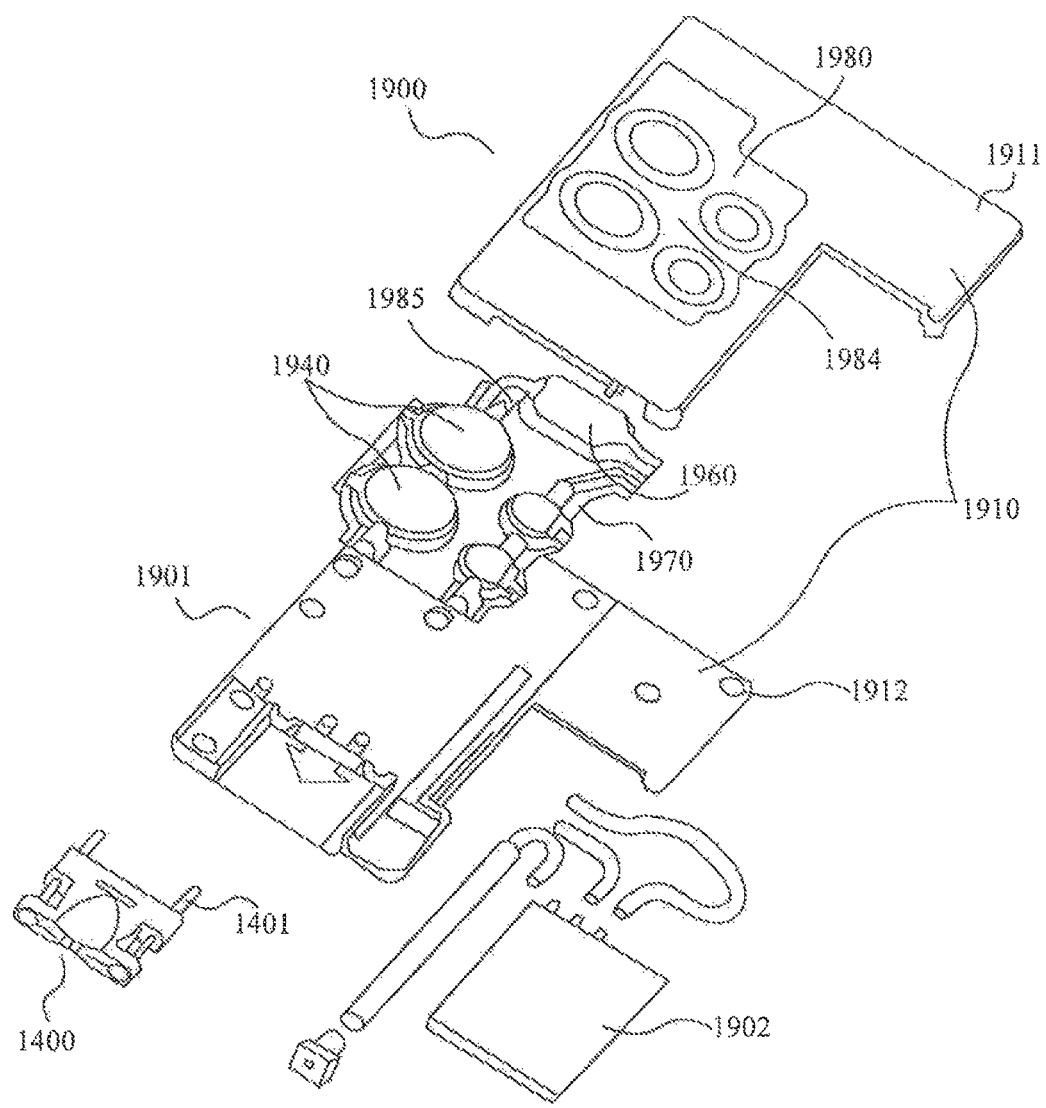
FIG. 17C illustrates a cartridge, according to an exemplary disclosed embodiment.

FIGS. 17B and 17C provide perspective views of a cartridge 1900, according to an exemplary disclosed embodiment. FIG. 17B shows an assembled view of cartridge 1900, and FIG. 17C shows an exploded view of cartridge 1900. Cartridge 1900 may include a preparation portion 1901 as well as an analysis portion 1902. As shown in FIG. 17C, cartridge 1900 may include a rigid frame or rigid portion 1910. Rigid portion 1910 may be fabricated (e.g., by molding or any other suitable technique) as a two-part structure. As shown, rigid frame 1910 may include a top portion 1910 configured to mate with and attach to a bottom portion 1912.

In some embodiments, rigid portion 1910 may include one or more inlets 1920, which may each be configured to receive, support, and/or align a fluid sampler, such as a capillary tube containing a quantity of sample fluid. Various flow paths may be fabricated into or on rigid portion 1910 to establish fluid flow paths within cartridge 1900. For example, any or all of the flow paths described above with respect to the cartridge of FIG. 17A may also be included in the two part rigid frame 1910 of FIG. 17C.

Cartridge 1900 may be fabricated not only with a two part rigid frame 1910, as shown in FIG. 17C, but also with two or more flexible sheets of material. For example, cartridge 1900 may include a first sheet 1970 and a second sheet 1980. In some embodiments, sheet layers 1970 and 1980 may include a flexible material (e.g., a polymer or any other suitable elastic material) and may be bonded together during fabrication of cartridge 1900. Any suitable techniques for bonding flexible materials together may be used. In some embodiments, different regions of layers 1970 and 1980 may be bonded together with varying bond strengths. Such configurations may be useful, for example, to permanently or semi-permanently bond together certain regions and more temporarily bond together other regions. For example, in some regions, a frangible seal may be formed by forming a temporary bond between layer 1970 and layer 1980 that can be peeled apart to open the seal.

Various mechanisms may be used to bond layers 1970 and 1980 together. For example, adhesives may be used, In some regions, such as region 1984, where permanent or semi-permanent bonds are desired, suitable adhesives may be used to permanently or semi-permanently bond together layers 1970 and 1980 in those regions. Similarly, other adhesives, e.g., those that provide only a temporary, peelable bond, may be used in other regions, such as region 1985 where a temporary bond may be desired in order to create a frangible seal.

Such bonding may also be accomplished through welding. For example, in some embodiments, an electrode may be used to create spot welds between layers 1970 and 1980. In such embodiments, a bond-strength between the two layers may depend on the density and/or shape of spot welds in a particular region. Thus, regions such as region 1984, where a high bond-strength may be desired, a higher density of spot welds may be used as compared to regions, such as region 1985, where a lower density of spot welds may be used in order to provide a temporary, peelable bond.

Layers 1970 and 1980 may also be bonded together via other mechanisms. For example, each of layers 1970 and 1980 may include two sub-films, such as a first sub-film having a lower melting or bonding temperature as compared to a second sub-film that has a higher melting or bonding temperature. Layers 1970 and 1980 may be formed such that during bonding, they are oriented such that the first sub-film from layer 1970 forms an interface with the first sub-film of layer 1980 and the second sub-films of each of layers 1970 and 1980 do not contact one another. To form a temporary, peelable bond, in a particular region, such as region 1985 at a frangible seal location, a low temperature may be applied (e.g., in the range of about 100 C to about 130 C) such that the first sub-films bond together. The bonded structure in this region may be later peeled apart by separation of the bonded first sub-films or by tearing a structure formed by the bonded, first sub-films. To create a permanent or semi-permanent bond, such as in region 1984, a higher temperature (e.g., in the range of about 140 C to about 180 C) may be applied. Such a temperature may cause the first sub-films to melt and/or flow away from the region to be bonded enabling the second sub-films of layers 1970 and 1980 to come in contact and form a permanent or semi-permanent bond. Such bonding techniques, including adhesives, spot welding, and/or multi-layered, temperature-dependent bonding structures may also be used in conjunction with any of the cartridges described herein.

Layers 1970 and 1980 may be prefabricated or formed to include various structures for providing flow paths, reservoirs, seals, etc. upon bonding of layers 1970 and 1980 together. For example, layers 1970 and 1980 once bonded together may form reservoirs 1940. These reservoirs may be flexible and, therefore, deformable in response to pressing (i.e., "pressable"). Similarly, layers 1970 and 1980 together may form frangible seals, e.g., in flow paths between reservoirs, compartments, etc. Such a frangible seal may include a seal in region 1985, as shown in FIG. 17C. Bonded layers 1970 and 1980 may form other structures, such as a buffer compartment 1960.

Activation Unit

Figure 18:
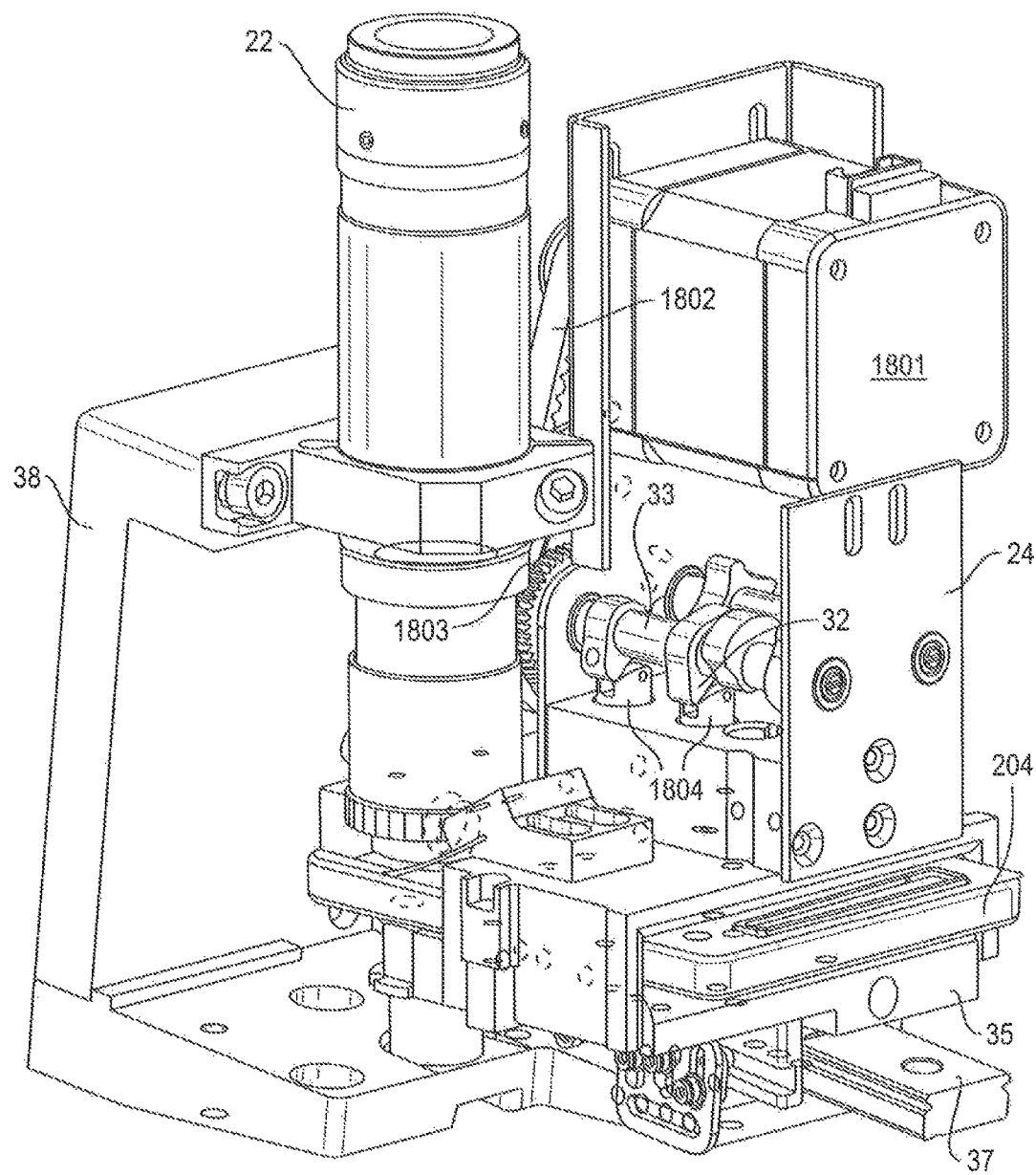
FIG. 18 provides a diagrammatic, perspective view representation of selected internal components of an analysis system, according to exemplary disclosed embodiments.

FIG. 18 provides a diagrammatic, perspective view representation of selected internal components of an analysis system, according to exemplary disclosed embodiments. As previously noted with respect to FIG. 3, and as further illustrated in FIG. 18, to prepare a sample included on cartridge 204, activation unit 24 may interact with one or more sections of cartridge 204 in order to prepare the fluid sample for analysis. In some embodiments, cartridge activation unit 24 may include one or more cams 32 incorporated on a rotating camshaft 33 turned by motor 1801, belt 1802, and gearing 1803 in order to press (either directly by contacting sections of the cartridge or indirectly by interacting with one or more pistons 1804 that contact the cartridge) sections of the cartridge to prepare, mix, move, distribute, etc. a fluid sample for analysis. Activation unit 24 may include more or few components than the cams, camshaft, motor, belt, pistons, and gearing described.

Cams 32 and/or pistons 1804 may be configured to interact with any suitable portions of cartridge 204 in order to prepare a fluid sample for analysis, transport fluid within portions of cartridge 204, open seals, etc. For example, cams and/or pistons 1804 may interact with any of the pressable portions, reservoirs, buffer chambers, compartments, fluid channels, etc. described above with respect to any of the various embodiments of cartridge 204. For example, as shown in FIG. 18, rotation of camshaft 33 may cause cams 32 to rotate. By virtue of the various shaped profiles of cams 32, for example, including different shaped lobes radially distributed about camshaft 33, cams 32 may press on pistons 1804 to depress pistons 1804 at various different times. The cam lobes may be arranged, for example, to cause pistons to alternately press on adjacent fluid reservoirs, as described above, in order to transfer fluid back and forth from one reservoir to another.

The following discussion provides additional details regarding various configurations of activation unit 24, including cams 32, camshaft 33, pistons 1804, and how activation unit 24 interacts with various sections of cartridge 204. For purposes of the disclosure, cams 32 are not limited to any particular structure or configuration. Cams 32 may include unitary elements or may include multiple separate components assembled together. Cams 32 may have any suitable thickness and any suitable configuration of lobes. Additionally, any number of camshafts 33 may be employed (e.g., one shaft, two, three, or more). Moreover, motor 1801 (or any other driver for activation unit 24) may be directly connected to camshaft 33 or may be indirectly attached to camshaft 33 through gearing, belts, etc. (as shown in FIG. 18). The activation unit driving mechanism (e.g., motor 1801) may include any driving mechanism suitable for causing a desired activation motion (e.g., rotating shafts). The driving mechanism may be configured for driving a rotating mechanism at fixed or variable speeds, and may change speeds and/or rotation direction during operation. Controller 20 may cause motor 1801 to rotate camshaft 33 in accordance with a predefined pattern adapted for a particular cartridge configuration.

Figure 19:
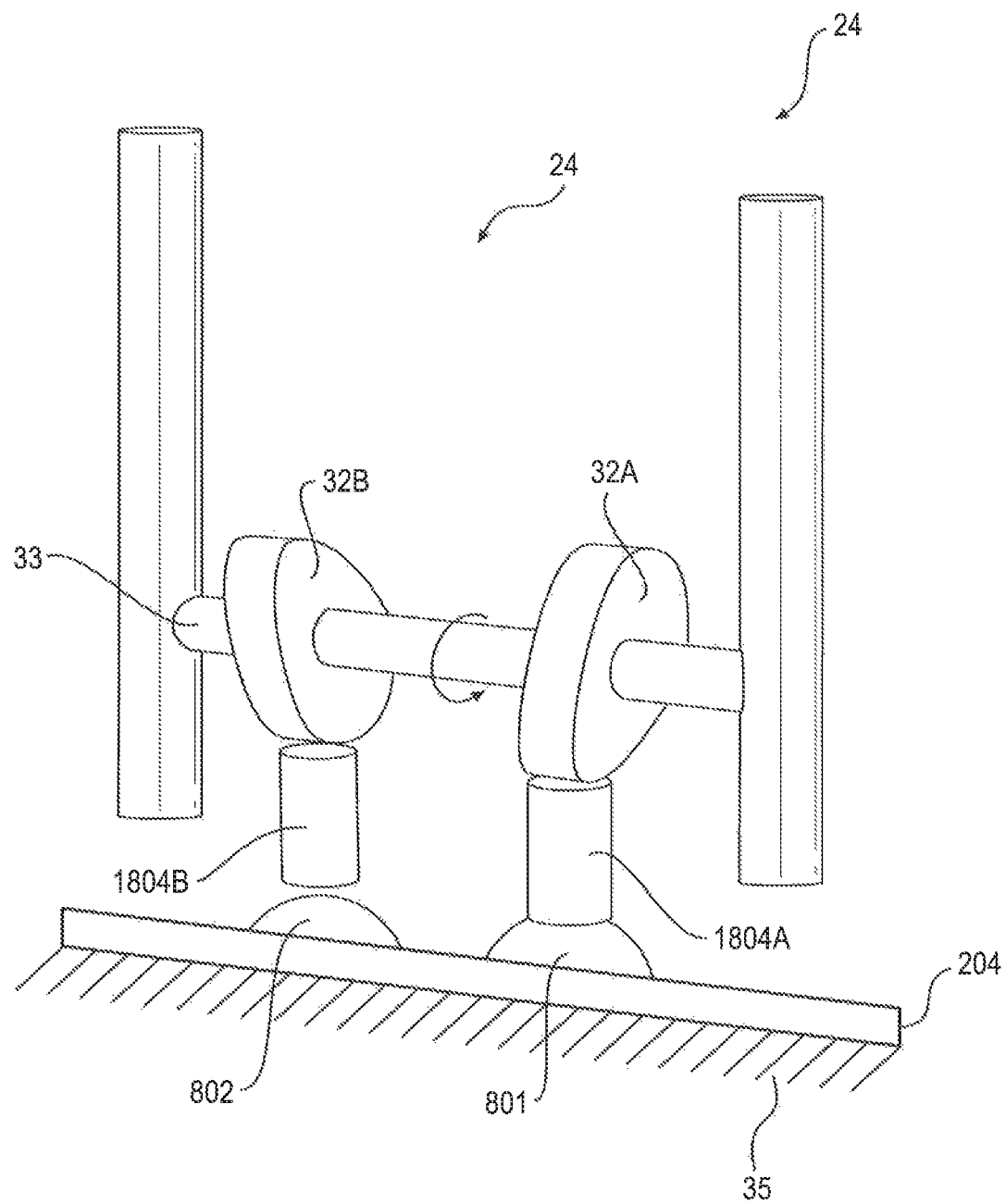
FIG. 19 provides a diagrammatic representation of an activation unit, according to exemplary disclosed embodiments.
Figure 20:
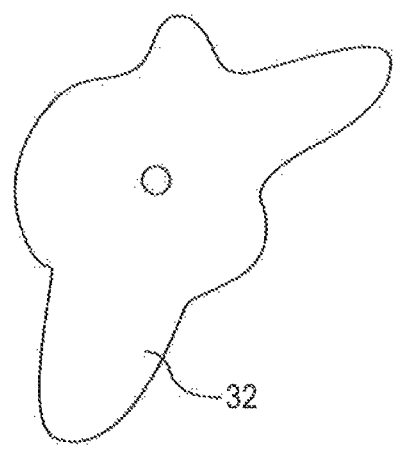
FIG. 20 provides a diagrammatic representation of a multi-lobed cam, according to exemplary disclosed embodiments.

Referring to FIG. 19, driving the camshaft 33 according to a predefined pattern in conjunction with a certain cartridge 204 including pressable elements (e.g., elements that cover or themselves constitute all or part of reservoirs 801 and 802 (FIG. 9)) results in timed pressing and releasing of the pressable elements in response to movements of cams 32. For example, as shown in FIG. 19, cam 32A has a lobe (or node) contacting piston 1804A causing piston 1804A to partially depress a pressable element associated with reservoir 801. Cam 32B has a similar profile to cam 32A, but has a different rotational position. As a result, the long lobe of cam 32B has not yet come into contact with piston 1804B. When camshaft 33 rotates sufficiently to cause cam 32B to contact piston 1804B (which will cause piston 1804B to move downward and press on a pressable element associated with reservoir 802), cam 32A will have rotated such that cam 32A no longer contacts piston 1804A. Continued rotation of camshaft 33, therefore, will cause periodic and sequential pressing of pressable elements associated with reservoirs 801 and 802, such that fluid may flow back and forth between reservoirs 801 and 802 as cams 32A and 32B rotate through repeated cycles. Of course, the arrangement shown in FIG. 19 is an example only. More or fewer cams may be included. More or few pistons (or no pistons) may be included, and activation unit 24 may be configured to depress or interact with any number of different structures associated with cartridge 204. Additionally, cams 32 may have any suitable profile. In some embodiments, any of cams 32 may include a single lobe (node), as shown in FIG. 19. In other embodiments, however, any of cams 32 may include multiple lobes (nodes) positioned at different radial locations, as shown in FIG. 20. Multiple cams 32 within activation unit 24 may be configured with the same or similar width. In other embodiments, cams 32 may include different widths.

In addition to causing pressure to be applied to pressable elements associated with reservoirs 801 and 802, cams 32A and 32B may be configured to cause pressure to other areas of cartridge 204. For example, in some embodiments, the cams may cause pressure to be applied to one or more fluid conduits associated with cartridge 204. Under such pressure, such fluid conduits may pinch shut in order to reduce or prevent the flow of fluid between two or more regions of cartridge 204.

Figure 21:
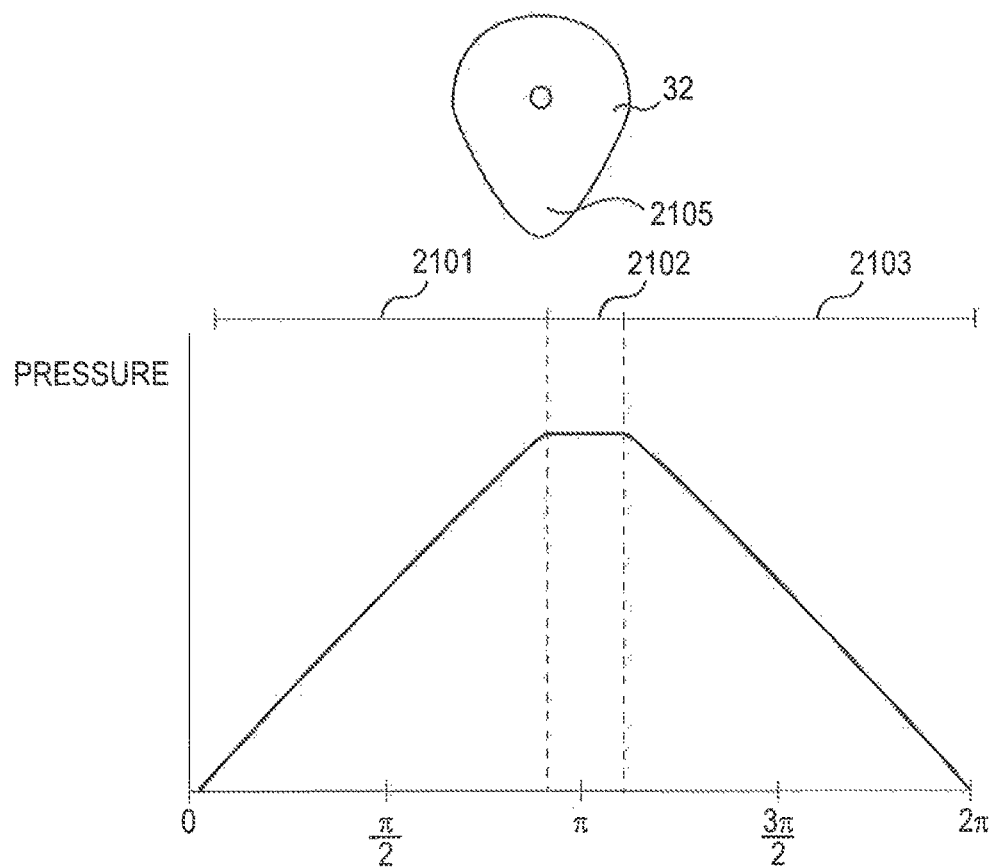
FIG. 21 provides a qualitative pressure diagram corresponding to the rotation of a cam, according to an exemplary disclosed embodiment.

Pressure diagrams can be associated with cams based on their node configurations. Such diagrams may reflect changes in pressure on a pressable element imparted by the nodes of a cam as it rotates. Such a qualitative pressure diagram is shown in FIG. 21, which provides a diagrammatic, qualitative representation of pressure imparted by a cam 32 on a pressable element over one complete cycle of rotation (360 degrees). The pressure diagram of FIG. 21 includes three pressure phases caused by the rotation of cam 32: a rising pressure phase 2101, a dwell pressure phase 2102, and a diminishing pressure phase 2103. The absolute value of the slope of the rising phase is not necessarily similar to the absolute value of the slope of the diminishing phase and depends on the profile of lobe 2105 of cam 32. As noted above, any of cams 32 included in activation unit 24 may be configured with any desired cam profile (e.g., lobe shape, lobe number, lobe amplitude, cam width, etc.) to provide a desired pressure profile at one or more particular locations of cartridge 204 (e.g., at the pressable members associated with reservoirs 801 and 801).

In addition to rotating a cam 32 through a full 360-degree cycle in order to apply pressure to a pressable element of cartridge 204, camshaft 33 may be rotated over a more limited angular range. For example, in some embodiments, a desired pressure profile may be obtained by rotating camshaft 33 and, therefore, cam 32 forward and backward over a portion of the full 360-degree range (e.g., over a ±10-degree range; a ±20 degree range; or larger or smaller range).

Positioning Unit

As noted above and referring back to FIG. 3, system 101 may also include a positioning unit 26. Positioning unit 26 may include various components for controlling the position of the prepared sample (e.g., on cartridge 204) relative to analysis components included in fluid analyzer 22. For example, in some embodiments, positioning unit 26 may include a motor 34 (or other suitable type of actuator) connected to a stage 35 via a shaft 36. Motor 34 may be used to rotate or otherwise move shaft 36 in order to move stage 35, on which cartridge 204 may be retained during analysis. Stage 35 may be mounted on an inclined rail 37, such that movement of shaft 36 (which may extend parallel to inclined rail 37) may either pull stage 35 up inclined rail 37 or push stage 35 down inclined rail 37. As a result of the movement along rail 37, stage 35 may simultaneously move both in the X direction and the Z direction relative to fluid analyzer 22. As shown in FIG. 3, the X axis extends in a direction substantially orthogonal to an analysis axis 27 of fluid analyzer 22, and the Z axis extends in a direction substantially parallel to the analysis axis of fluid analyzer 22. In some cases, e.g., where fluid analyzer 22 includes a imaging device such as a camera, analysis axis 27 may correspond to an optical axis of the imaging device. Positioning unit 26 may include more or fewer components than the motor and shaft described herein for moving stage 35.

Movement of stage 35 along inclined rail 37 may cause a corresponding movement of cartridge 204 residing on or retaining against stage 35. In some embodiments, stage 35 may be configured with a top surface (or a sample supporting surface) that is substantially perpendicular to analysis axis 27 of fluid analyzer 22 (and the Z direction) and substantially parallel to the X direction (see FIG. 3). Thus, in some embodiments, when cartridge 204 is placed on stage 35, cartridge 204 may be arranged such that an analysis region of cartridge 204 (e.g., micro channel 1003) extends along the X direction and perpendicular to analysis axis 27.

As shown in FIG. 3, inclined rail 37 may be included relative to the X direction. Thus, movement of stage 35 along inclined rail 37 may cause translation of cartridge 204 in both the X and Z directions relative to analysis unit 22. In other words, movement of stage 35 along inclined rail 37 may result in a first component of motion for stage 35/cartridge 204 in the X direction (perpendicular to analysis axis 27) and a second component of motion for stage 35/cartridge 204 in the Z direction (parallel to analysis axis 27). As a result of the motion in the Z direction parallel to analysis axis 27, at least a portion of the prepared sample on cartridge 204 may be brought into focus relative to analysis components of fluid analyzer 22. In embodiments where fluid analyzer 22 includes one or more imagers, such focus may include optical focus.

Any suitable type of movement mechanism may be employed in positioning unit 26 to move stage 35 along inclined rail 37. In some embodiments, positioning unit 26 may include a motor 34. In some cases, motor 34 may include a stepper motor, which may offer the benefits of precision and repeatability. Other types of movement devices may be used, such as servo motors, DC motor encoders, etc. As noted, motor 34 may be coupled to a shaft 36 (either directly or indirectly through one or more coupling components), which, in turn, may be coupled to stage 35 (either directly or indirectly through one or more coupling components). In some embodiments, shaft 36 may interface with stage 35, for example, via threads or a threaded component. In such embodiments, motor 34 may cause shaft 36 to turn through a desired angle of rotation in order to cause a desired amount of translation of stage 35 along inclined rail 37 (via threads on shaft 36 interacting with corresponding threads included in stage 35 or a component associated with stage 35, for example).

Such an arrangement may offer the benefit of providing precision control over sample focusing without requiring similarly precise motors. For example, in an embodiment where a motor or other type of actuator moves a sample directly along the optical axis of an imager to focus the sample relative to the imager, the precision in the focus adjustment may depend on the precision offered by the motor or actuator. And, in applications where micron or sub-micron resolution may be desirable, motors or actuators providing the required level of precision may be costly.

in the presently disclosed embodiments, however, micron or sub-micron resolution may be achieved with motors or actuators that otherwise would not be capable of providing such resolution if configured to move a sample directly along an optical or analysis axis of the analysis unit 22. For example, using the disclosed inclined rail arrangement, a translation of stage 35 along inclined rail 37 sufficient to cause R mm of horizontal movement (along the X direction, as shown in FIG. 3) will induce an R×S mm movement in the Z direction (FIG. 3) (where S is the slope ratio associated with the inclined rail). For example, in a case where linear rail 37 is configured with a 1/10 slope ratio (S), a translation of stage 35 along inclined rail 37 sufficient to cause 6 microns of horizontal movement (R) in the X direction will result in 0.6 microns of movement in the Z direction. Thus, by leveraging the slope of the inclined rail, the effective vertical focusing precision may be increased significantly (e.g., by a factor of 2, 5, 10, or even higher) over the precision of the motor or other actuator.

While the disclosed system may result in movement along the X axis in addition to the movement along the Z axis used for focusing, such horizontal translation may be inconsequential for a wide range of applications. For example, in some embodiments, a fluid inspection area on cartridge 204 may include a micro channel 1003 (as shown in FIGS. 11, 13, 14A, or 14B). Using the viscoelastic focusing technique described above, cells or particles suspended in a viscoelastic medium and flowing through a micro channel 1003 (e.g., having a length of greater than 100 microns and at least one cross-sectional dimension less than 100 microns, e.g., between 5 microns and 100 microns) may become physically focused or aligned into a single plane. Arrangement of the flowing cells into a single plane may facilitate acquisition of images of the flowing cells by a camera associated with analysis unit 22, for example. Such images may be analyzed for performing cell counts.

Flowing the particles or cells to be analyzed along a micro channel may also facilitate the use of the focusing arrangement described above. For example, because the flowing cells may be physically focused in a plane that extends along micro channel 1003, analysis may be performed of the cells at any location along a length of the micro channel where the flowing cells are suitably arranged. For example, in some embodiments, the micro channel may be about 1 mm wide, 40 microns deep, and 20 mm long (of course, any other suitable dimensions could be used, especially if they allow for a viscoelastic focusing effect). After entering micro channel 1003, the cells or particles may align (by viscoelastic focusing, for example) within a short distance of entering the micro channel. For example, in some embodiments, the physical focusing of the cells or particles may occur within 5 mm or less or 3 mm or less from an inlet to the micro channel, and they may remain focused as they flow over the remaining length of the micro channel. The focused cells may align in a plane approximately 20 microns above the bottom of the micro channel 1003 where the micro channel has a depth of 40 microns. In order to inspect the cells or particles, analysis unit 22 may be positioned anywhere along the inspection region, such as the micro channel, where the cells or particles to be analyzed exhibit an arrangement suitable for analysis in the viscoelastic focusing example described, analysis unit 22 including, e.g., a camera or other type of imager may be positioned anywhere along micro channel 1003 such that the field of view of the camera or imager overlaps with an area where the cells or particles to be analyzed are viscoelastically focused into a single plane. For example, assuming a field of view of about 0.3 mm×0.3 mm, images of the viscoelastically focused cells or particles may be acquired anywhere along the micro channel where the cells or particles are focused. This may include a region anywhere within the 1 mm width of the channel and anywhere from about 3 mm downstream of the channel inlet to the channel outlet, which in the example described above is about 20 mm from the inlet. Because the cells or particles may be flowing, collecting images at different locations along the micro channel may be inconsequential, as the cells captured from image to image would be changing anyway as a result of the flow.

This flexibility in locating a suitable analysis site is compatible with the focusing system described above, which may include at least some horizontal (X direction) translation along with movements for focusing in the vertical direction (Z). In some cases, the horizontal direction of travel of the stage 35 along inclined rail 37 may be aligned with a micro channel or other inspection area included on cartridge 204. Thus, as stage 35 translates along inclined rail 37, analysis unit 22 may follow the path of the micro channel or other inspection area. In a particular example, as stage 35 and cartridge 204 move along inclined rail 37 relative to analysis unit 22, images of a field of view of 0.3 mm×0.3 mm may be taken over a 5 mm length of micro channel 1003 having a width of 1 mm. Assuming a 1/10 slope factor ratio for inclined rail 37, a 5 mm image capture zone along micro channel 1003 may allow for up to 500 microns of Z movement, which may be more than sufficient to enable optical focusing at any location over the entire micro channel depth (e.g., of about 30-40 microns) or substantially beyond.

The presently disclosed embodiments may also include an autofocus function. For example, where analyzer unit 22 includes a camera or imager, positioning unit 26 may be controlled by controller 20 to automatically move stage 35 as part of an autofocus process for optically focusing imaging components associated with analyzer unit 22 upon an area of interest of the fluid to be analyzed. In some embodiments, controller 20 may cause the imaging components of analyzer unit 22 to achieve an optical focus coinciding with the location of a viscoelastically focused area of cells within micro channel 1003.

The autofocus process may proceed according to any suitable process for achieving a desired level of focus relative to the cells or particles to be analyzed. In some embodiments, the autofocus process may proceed by collecting images with analyzer unit 22 at a series of positions along the Z axis (by translating stage 35 along inclined rail 37). For example, stage 35 may be translated along inclined rail 37 such that stage moves over a range of 100 microns in the Z direction (or any other suitable distance). Images may be acquired every 2 microns in the Z direction (or at any predetermined distance interval along the rail or at any other suitable interval). The images collected at the various Z locations may be analyzed (with controller 20, for example) to determine a focus level or quality with respect to the cells or particles of interest. In some embodiments, the analysis may include the evaluation of mathematical criteria (e.g., a spatial frequency analysis) that may be indicative of the focus quality at a particular Z position. In some embodiments, higher spatial frequencies may indicate higher focus quality, and lower spatial frequencies may indicate lower focus quality. Based on the scan over the various Z locations/rail locations and analysis of images captured there, the location (e.g., a target location) corresponding to the highest quality observed focus may be determined. To conduct the desired fluid analysis (e.g., cell count, etc.), controller 20 may reposition stage 35 at the target location determined to correspond to the highest observed focus quality.

Additionally, rather than simply moving the stage to the target location initially determined as having the highest observed focus quality and then performing fluid analysis at that location, one or more subsequent scans may be performed. For example, after the first scan over various Z directions, one or more additional scans may be performed, for example, over increasingly fine movements in the Z direction around the previously determined target location of the highest focus quality, in order to refine the level of focus on the cells or particles of interest. Each subsequent scan may result in a new target location being determined. Such subsequent scans may include Z direction steps of 1.5 microns, 1 micron, 0.5 microns, or less, for example.

In addition to or as an alternative to this iterative autofocusing approach involving a plurality of scans over various Z positions, controller 20 may also calculate a Z position expected to offer the highest focus quality based on a single scan of Z locations. For example, in such a process, the autofocus process may proceed by collecting images with analyzer unit 22 at a series of positions along the Z axis (by translating stage 35 along inclined rail 37). The images collected at the various Z locations/rail locations may be analyzed (with controller 20, for example) to determine a focus level or quality with respect to the cells or particles of interest. The focus quality levels at the various Z locations/ rail locations may be used to predict the Z location/location of the highest quality of focus. For example, controller 20 may extrapolate a highest focus quality Z location/rail location (e.g., the target location) based on the observed focus quality values, may use curve fitting techniques, or any other suitable type of calculation to predict the Z location expected to offer the highest focus quality. Once this target location is determined controller 20 may reposition stage 35 along inclined rail 37 such that the stage is positioned at the calculated target location.

It should be noted that the determined Z location offering the highest focus quality (whether observed or calculated) may or may not correspond to any particular distance between analyzer unit 22 and cartridge 204, stage 35, or the cells to be analyzed. Rather, in some cases, the determined Z location offering the highest focus quality may correspond only to a value tracked by controller 20 relative to the operation of positioning system 26. In other words, controller 26 may not determine any actual vertical distance Z between any part of the analyzer unit and any part of the cartridge or fluid contained therein. Rather, controller 20 may track the position of motor 34 and use this as the basis for tracking observed focus quality values. As each unique motor position, however, may correspond to a unique Z position of cartridge 204, for example, all references in this disclosure to tracked Z position, determined Z position, etc. should be understood as synonymous with tracking, determining, etc. a motor position or any other quantity controller 20 may use to index the movement of stage 35 along inclined rail 37. For example, motion of motor 34 may result in corresponding motion of stage 35 L along inclined rail 37, such that motor position may enable determination of a position of stage 35 along inclined rail 37. Movement of stage 35 (and, therefore, cartridge 204) in the Z direction as a result of a translation L along the inclined rail 37 may be expressed as $Z=L*\sin(\alpha)$. At small angles of inclination, tangent is approximately equal to sin, and, therefore, at small angles, the inclination ratio S is approximately $\sin(\alpha)$. Accordingly, at small angles of inclination, Z (the component of motion of the stage/cartridge) in the Z direction parallel to analysis axis 27 is approximately equal to the translation, L, along the inclined rail multiplied by S, the inclination ratio.

In some embodiments, the analysis may include the evaluation of suitable mathematical criteria (e.g., a spatial frequency analysis) that may be indicative of the focus quality at a particular Z position. In some embodiment, higher spatial frequencies may indicate higher focus quality, and lower spatial frequencies may indicate lower focus quality. Based on the scan over the various Z locations and analysis of images captured there, the location of the highest quality focus may be determined. To conduct the desired fluid analysis (e.g., cell count, etc.), controller 20 may reposition stage 35 at the location determined to correspond to the highest observed focus quality.

The disclosed system may also include an autofocus validation step. For example, as noted above, based on observed focus quality values at various Z positions/rail positions, a target position may be calculated. The calculated target position may correspond to the Z position/rail position expected to provide the highest quality focus. To validate the calculation, controller 20 may position stage 35 at the desired Z location/rail position, collect an image via analysis unit 22, analyze the collected image, and determine whether the focus quality is as expected.

in the disclosed system, certain systems may be associated with one another to provide at least some level of mechanical isolation. For example, as shown in FIGS. 3 and 18, analyzer unit 22 may be mounted or coupled to a frame 38, to which motor 34 and inclined rail 37 are also coupled. Stage 35 and activation unit 24, however, are not coupled to the frame 38. Rather, both are free to slide together along the inclined rail 37 under the influence of motor 34 and shaft 36, for example.

As a result of this configuration, potential effects on the fluid analysis from the motion of various components in activation unit 24 may be reduced or eliminated. For example, by mechanically coupling together stage 35 and activation unit 24, the motion of cams 32 and/or pistons 1804 may operate to exert a downward force on the cartridge 204, which may be translated to stage 35. Because activation unit (including cams 32 and pistons 1804) are mounted together with stage 35, however, no force from the motion of cams 32 and/or pistons 1804 is transferred to the linear rail 37. This can be beneficial because, any force exerted on the rail could potentially damage the rail or impede the motion of stage 35 along the rail. Moreover, any forces not remaining internal to the cartridge/stage/activation unit system could cause relative motion between the cartridge and the analyzer unit 22 and, therefore, impact or change the focus of analyzer unit 22 relative to the fluid within cartridge 204, which could hinder the fluid analysis.

It will be apparent to those skilled in the art that various modifications and variations can be made in the disclosed fluid analysis system without departing from the scope of the disclosure. Other embodiments of the disclosed systems and methods will be apparent to those skilled in the art from consideration of the specification and practice of the disclosure disclosed herein.

What is claimed is:

1. A fluid analysis system, comprising:
   a stage configured to receive a sample holder including a fluid sample to be analyzed; and
   an activation unit including a rotatable camshaft and one or more cams associated with the camshaft, wherein the one or more cams are configured to:
      cause at least some movement of fluid associated with the sample holder upon rotation of the camshaft, the fluid including at least some of the fluid sample to be analyzed; and
      cause the fluid to flow back and forth between a first fluid reservoir on the sample holder and a second fluid reservoir on the sample holder by alternatingly pressing on a first pressable portion associated with the first fluid reservoir and a second pressable portion associated with the second fluid reservoir upon rotation of the camshaft.

2. The fluid analysis system of claim 1, wherein the one or more cams are further configured to cause simultaneously pressing on the first pressable portion associated with the first fluid reservoir and on the second pressable portion associated with the second fluid reservoir, upon rotation of the camshaft, such that a pressure against a breakable seal on the sample holder is caused to exceed a breaking threshold of the breakable seal in order to output at least some of the fluid through the breakable seal.

3. The fluid analysis system of claim 1, wherein the one or more cams associated with the camshaft directly contact respective ones of the first pressable portion and the second pressable portion.

4. The fluid analysis system of claim 1, wherein the one or more cams associated with the camshaft interact with the first pressable portion and the second pressable portion via pistons.

5. The fluid analysis system of claim 1, wherein at least one of the one or more cams has only a single lobe.

6. The fluid analysis system of claim 1, wherein at least one of the one or more cams has multiple lobes.

7. The fluid analysis system of claim 1, further including a motor, wherein the motor is configured to turn the camshaft.

8. The fluid analysis system of claim 7, wherein the motor is configured to turn the shaft at variable speeds during operation.

9. The fluid analysis system of claim 7, wherein the motor is configured to turn the shaft in different directions during operation.

10. A fluid analysis system, comprising:
a stage configured to receive a sample holder including a fluid sample to be analyzed; and
an activation unit including a rotatable camshaft and one or more cams associated with the camshaft, wherein the one or more cams are configured to:
cause at least some movement of fluid associated with the sample holder upon rotation of the camshaft, the fluid including at least some of the fluid sample to be analyzed;
cause the fluid to flow within a fluid reservoir on the sample holder by alternatingly pressing and releasing a pressable portion of the fluid reservoir upon rotation of the camshaft; and
cause application of a first pressure to the pressable portion of the fluid reservoir, upon rotation of the camshaft, such that a second pressure against a breakable seal on the sample holder is caused to exceed a breaking threshold of the breakable seal in order to output at least some of the fluid through the breakable seal.

11. The fluid analysis system of claim 10, wherein at least one of the one or more cams associated with the camshaft directly contacts the pressable portion of the fluid reservoir.

12. The fluid analysis system of claim 10, wherein at least one of the one or more cams associated with the camshaft interacts with the pressable portion via a piston.

13. The fluid analysis system of claim 10, wherein at least one of the one or more cams has multiple lobes.

14. The fluid analysis system of claim 10, further including a motor, wherein the motor is configured to turn the camshaft.

15. The fluid analysis system of claim 14, wherein the motor is configured to turn the shaft at variable speeds during operation.

16. The fluid analysis system of claim 14, wherein the motor is configured to turn the shaft in different directions during operation.

* * * * *